United States Patent [19]
Grönberg et al.

[11] Patent Number: 6,083,733
[45] Date of Patent: Jul. 4, 2000

[54] THERMOSTABLE XYLANASES

[75] Inventors: Vidar Grönberg, Gilstead Bingley; Simon Forster, Leeds; Dean Moody, Huddersfield, all of United Kingdom; Diane P. Williams; Sara Iverson, both of Hopkinton, Mass.; Roberta Lee Farrell, Hamilton, New Zealand; Peter Leonard Bergquist, Chatswood, Australia; McIver Daniel; Hugh William Morgan, both of Hamilton, New Zealand; Wilhelmus Johannes Quax, Voorschoten, Netherlands; Margareta Adriana Herweijer, Den Haag, Netherlands; Brian Edward Jones, Leidschendam, Netherlands

[73] Assignee: Gist-brocades B.V., Netherlands

[21] Appl. No.: 08/591,685

[22] PCT Filed: Jun. 14, 1995

[86] PCT No.: PCT/EP95/02299

§ 371 Date: Feb. 5, 1997

§ 102(e) Date: Feb. 5, 1997

[87] PCT Pub. No.: WO95/34662

PCT Pub. Date: Dec. 21, 1995

[30] Foreign Application Priority Data

Jun. 14, 1994 [EP] European Pat. Off. .............. 94201699

[51] Int. Cl.[7] .............. C12N 9/24; C12N 1/00; D21C 1/00; D01C 1/04
[52] U.S. Cl. .......... 435/200; 435/277; 435/278; 435/822; 435/252.1; 530/412
[58] Field of Search ................... 435/200, 277, 435/278, 822, 252.1; 530/412

[56] References Cited

FOREIGN PATENT DOCUMENTS

| 0 511 933 A2 | 4/1992 | European Pat. Off. . |
| 0 538 177 A1 | 10/1992 | European Pat. Off. . |
| WO 93/19171 | 3/1993 | WIPO . |
| WO 95/12668 | 11/1994 | WIPO . |

OTHER PUBLICATIONS

Ruttersmith, R.M., et al., Cellulolytic and Hemicellulolytic Enzymes Functional Above 100°C; *Annals of NY Acad. of Sci.*, pp. 137–141, vol. 672 (Enzyme Engineering XI), (1992).

Sakka, K., et al., Nucleotide Sequence of the *Clostridium stercorarium* xynA Gene Encoding Xylanase A: Identification of Catalytic and Cellulose Binding Domains; *Biosci, Biotech. Biochem.* (1993) 57:273–277.

Sakka, K. et al., Cloning and Expression in *Escherichia coli* of *Clostridium stercorarium* Strain F–9 Genes Related to Xylan Hydrolysis, *Agric. Biol. Chem.* (1990), 54:337–342.

Irwin, D., Characterization and Sequence of a *Thermomonospora fusca* Xylanase, *App. Envir. Micro.* (1994) p. 763–770.

*Primary Examiner*—Rebecca E. Prouty
*Attorney, Agent, or Firm*—Morrison & Foerster LLP

[57] ABSTRACT

The present invention discloses enzymes having xylanase activity. The xylanases are characterized in that they are active at a temperature of 80° C. or higher. The enzymes are obtainable from anaerobic thermophilic bacteria. The enzymes are suited for use in paper and pulp production processes. The invention also describes cloning and expression of genes having xylanase activity obtained from the deposited strains.

12 Claims, 17 Drawing Sheets

```
TG457   .CGCTGCTTTGGTATCCTTCCACACAGAGTGTAATCTGGTCAATTGTACC
TG457   CCGCTGCTTTGGTATCCTTCCACACAGAGTGTAATCTGGTCAATTGTACC
TG457   CCGCTGCTTTGGTAGCCTTCCACACAGAGTGTAATCTGGTCAATTGTACC
TG53    CCGCTACTTTGGTAACCTTCAACGCAAAGAGTAATCTGATCGATTGTACC
TG53    .CGCTGCTTTGGTATCCTTCAACGCAAAGAGTAATCTGATCGATTGTACC
TG53    ................CTTCAACGCAAAGAGTAATCTGATCGATTGTACC 51                                              100
TG457   CAGGTtCAAACCTTTTGCAGCCCATGCTTTGAAATGATCAGTTACAGTAA
TG457   CAGGTtCAAACCTTTTGCAGCCCATGCTTTGAAATGATCAGTTACAGTAA
TG457   CAGGTTCAAACCTTTTGCAGCCCATGCTTTGAAATGATCAGTTACAGTAA
TG53    AAGATTCAAACCTTTTGCAGCCCATGCCTTGAAATGATCTGTAACTGTTA
TG53    AAGATTCAAACCTTTTGCAGCCCATGCCTTGAAATGATCTGTAACTGTTA
TG53    AAGATTCAAACCTTTTGCAGCCCATGCCTTGAAATGATCTGTAACTGTTA 101                                             150
TG457   CAGTACCACtTGTTCTCTTTGATGTCCTAACACTCCAGTACTGATCAAAT
TG457   CAGTACCACtTGTTCTCTTTGATGTCCTAACACTCCAGTACTGATCAAAT
TG457   CAGTACCACTTGTTCTCTTTGATGTCCTAACACTCCAGTACTGATCAAAT
TG53    CTGTACCGCTGGTTCTCTTCGAGGTTCTAACGCTCCAGTATTGATCAAAT
TG53    CTGTACCGCTGGTTCTCTTCGAGGTTCTAACGCTCCAGTATTGATCAAAT
TG53    CTGTACCGCTGGTTCCCTTCGAGGTTCTAACGCTCCAGTATTGATCAAAT 151                                             200
TG457   GTTCTTGTTCCTTCGATAGATGGCTGATTAACACGAGTTGTCTTATAAAT
TG457   GTTCTTGTTCCTTCGATAGATGGCTGATTAACACGAGTTGTCTTATAAAT
TG457   GTTCTTGTTCCTTCGATAGATGGCTGATTAACACGAGTTGTCTTATAAAT
TG53    GTTGTTGTCCCTTCAATAGATGGTTGATTTACACGAGTTGTCTTGTAAAT
TG53    GTTGTTGTCCCTTCAATAGATGGTTGATTTACACGAGTTGTCTTGTAAAT
TG53    GTTGTTGTCCCTTCAATAGATGGTTGATTTACACGAGTTGTCTTGTAAAT 201                                             250
TG457   ATCATATGTTCCTCCATCAATTGTTACAGTGCCAAGTGACGTTGCCCCGG
TG457   ATCATATGTTCCTCCATCAATTGTTACAGTGCCAAGTGACGTTGCCCCGG
TG457   ATCATATGTTGCTCCATCAATTGTTACAGTGCCAAGTGACGTTGCCCCGG
TG53    ATCATATGTTCCTCCATCGATTGTTACAGTACCAAGTGATGTTGCTCC.G
TG53    ATCATATGTTCCTCCATCGATTGTTACAGTACCAAGTGATGTTGCTCCGG
TG53    ATCATATGTTCCTCCATCGATTGTTACAGTACCAAGTGATGTTGCTCCGG
```

FIG.2A

```
        251                                             300
TG457   GCGGACGCCATGAGCCCCAGCTTTCAACGATATaAAATTCAACAAGTGGA
TG457   GCGGACGCCATGAGCCCCAGCTTTCAACGATATaAAATTCAACAAGTGGA
TG457   GCGGACGCCATGAGCCCCAGCTTTCAACGATATAAAaTTCAACAAGTGGA
TG53    GCGGACGCCATGAACCCCAGCTTTCAACAATATAGAATTCAACAAGTGGA
TG53    GCGGACGCCATGAACCCCAGCTTTCAACAATATAGAATTCAACAAGTGGA
TG53    gCGGACGCCATGAACCCCAGCTTTCAACAATATAGAATTCAACAAGTGGA 301               329
TG457   T.................................
TG457   TTTCTTGACCaTC.....................
TG457   TTTCTTGACCATCCATATACAcCCAA........
TG53    TTTCTTGACCATCCATAGAArCCCATATA
TG53    TTTCTTGACCATCCAT..............
TG53    TTTCTTGACCATCCATATACAGCCACATA
```

FIG.2B

```
         10        20        30        40        50        60
ACGAAACGAAGCATTGGCGCCTCGAGTAATTTACCAACACTACTACGTTTTAACTGAAAC 70        80       90SpHI    100       110       120
AAACAAACTGGAGACTGCCATGGCATATGGCATGCCATTTACCTCTAATGCAACTGGGAC
                                +  P  F  T  S  N  A  T  G  T 130       140       150       160       170       180
ATACGATGGTTACTACTACGAGTTGTGGAAGGACACAGGGAATACTACCATGACAGTTGA
 Y  D  G  Y  Y  Y  E  L  W  K  D  T  G  N  T  T  +  T  V  D 190       200       210       220       230       240
CACAGGAGGAAGATTTAGCTGTCAGTGGAGTAACATTAACAATGCACTCTTCAGAACAGG
 T  G  G  R  F  S  C  Q  W  S  N  I  N  N  A  L  F  R  T  G 250       260       270       280       290       300
TAAAAAGTTTAGCACTGCATGGAATCAGCTTGGGACTGTAAAGATTACCTACTCTGCTAC
 K  K  F  S  T  A  W  N  Q  L  G  T  V  K  I  T  Y  S  A  T 310       320       330       340       350       360
CTACAATCCAAATGGCAATTCCTATCTCTGCATTTATGGATGGTCAAGAAATCCACTTGT
 Y  N  P  N  G  N  S  Y  L  C  I  Y  G  W  S  R  N  P  L  V 370       380       390       400       410       420
TGAATTTTATATCGTTGAAAGCTGGGGCTCATGGCGTCCGCCCGGGGCAACGTCACTTGG
 E  F  Y  I  V  E  S  W  G  S  W  R  P  P  G  A  T  S  L  G 430       440       450       460       470       480
CACTGTAACAATTGATGGAGCAACATATGATATTTATAAGACAACTCGTGTTAATCAGCC
 T  V  T  I  D  G  A  T  Y  D  I  Y  K  T  T  R  V  N  Q  P 490       500       510       520       530       540
ATCTATCGAAGGAACAAGAACATTTGATCAGTACTGGAGTGTTAGGACATCAAAGAGAAC
 S  I  E  G  T  R  T  F  D  Q  Y  W  S  V  R  T  S  K  R  T
```

FIG.3A

THERMOSTABLE XYLANASES

TECHNICAL FIELD

The present invention relates to novel microorganisms and to novel enzymes. More specifically, the enzymes are thermostable xylanases. These xylanases are obtainable from anaerobic thermophilic bacteria. The xylanases are applicable under conditions used in the paper and pulp industry i.e. a pH of above 9 and a temperature of above 70° C., specifically the enzymes are active at T=80° C.

BACKGROUND OF THE INVENTION

Xylan is a component of plant hemicellulose. Xylan consists of a backbone of 1,4-glycosidically linked β-D-xylose. Usually xylans have side chains or groups comprising xylose and other pentoses, hexoses, uronic acids and acetyl groups.

In the paper production process the bleaching of pulp is an important step. Schematically, the process used for pulp treatment in the paper and pulp industry is performed as follows: Pulp is treated at pH 10–12 at 80° C. to remove most of the lignin in the so-called oxygen delignification step. The remaining pulp contains 2–5% of lignin. This lignin gives the pulp its brown color. Subsequently, the pulp is bleached in a multistage bleaching process. In this bleaching process chemicals such as chlorine, chlorine dioxide, hydrogen peroxide and/or ozone are used, to obtain a bright pulp for high quality paper.

Chlorine and chlorine-containing chemicals are often used in the bleaching process. However, since the use of these chemicals leads to the formation of dioxin and other chlorinated organic compounds, they form a threat to the environment. Therefore, there is a growing tendency to omit the use of chemicals giving rise to this kind of waste products.

This has prompted a tendency to develop chlorine-free processes; total chlorine-free (TCF) and elementary chlorine-free (ECF). In these processes hydrogen peroxide or ozone is used for bleaching. However, the use of these oxidative chemicals may have a negative effect on the quality of the paper, especially the strength of the paper It has been found that certain enzymes make the pulp more accessible to bleaching agents, thereby reducing the amount of bleach. Xylanases, in particular, have been found to be very useful in the paper and pulp processing. Xylanases have been reported to increase the extractability of lignins from the pulp. In current processes, xylanases are mostly used after the oxygen delignification step, because they are not active and do not survive under conditions used during oxygen delignification.

Xylanases cleave the hemicellulose chains which are responsible for the close adherence of lignin to the cellulose network. After xylanase treatment the lignin is more easily removed in the subsequent steps.

Therefore the use of xylanases leads to a reduction of the consumption of active chlorine in prebleaching of 25–30%. This reduction of chlorine does not afflict the quality parameters of the resulting paper (Viikari et al. 1986. Proc. of the third Int. Conf. Biotechnology in Pulp and Paper Ind., Stockholm, p.67–69 and Bajpai and Bajpai. 1992. Process Biochemistry. 27:319–325).

The xylanase treatment also reduces the need for other chemicals, such as hydrogen peroxide, in the bleaching process.

The use of xylanases from fungal sources in bleaching of kraft pulp has been reported. These are acidic xylanases and the pH and temperature optima of the enzymes are: pH 3-5 and T 30–50° C. These values are not ideal for the use in the bleaching process, where the prevailing conditions; are pH≧9 and temperature ≧70° C.

Xylanases from bacterial origin, with higher pH and/or temperature optima, have been reported for use in the bleaching process. Some of these originate from the following species (pH and temperature optima of the reported xylanase activity between brackets):

*Bacillus pumilus* (pH=7-9, T =40° C., Nissen et al. 1992. Progress in Biotechnology 7:325–337), *Bacillus stearothermoohilus* (pH=7, T=65° C. International patent application WO 91/10724), *Dictyoglomus thermophiluim* (pH=6-8, T=70° C., European patent application EP 0 511 933), *Rhodothermus* (pH=5.5–6.5, T=80–100° C., European patent application EP 0 538 177), *Thermotoga* (pH=5-6, T=90° C., International patent application WO 93/19171) and *Thermoanaerobacter ethanolicus* (T=68° C., Deblois and Wiegel. 1992. Progress in Biotechnology 7:487–490).

Although the use of some of these xylanases for bleaching has been claimed, no xylanases have been reported to date having the desired characteristics of significant delignification activity at temperature ≧80° C.

SUMMARY OF THE INVENTION

The present invention discloses xylanases obtainable from anaerobic thermophilic microorganisms which have been isolated in pure culture from hot springs in New Zealand. The microorganisms have been deposited at the Centraal Bureau voor Schimmelcultures (CBS), Baarn, the Netherlands, on Apr. 14, 1994.

The present invention also discloses enzymes having substantial xylanase activity at a temperature of at least 80° C. Furthermore, the present invention discloses that said xylanases possess significant delignification activity at a temperature of at least 80° C. Said enzymes are obtainable from the deposited strains.

The present invention further describes a process for the preparation of the xylanases which are active at a temperature of 80° C. The process comprises cultivation of the deposited microorganisms of the present invention in a suitable medium, followed by recovery of the enzymes having the indicated activity.

The present invention also discloses the cloning of the genes encoding the subject xylanases. Expression of these genes in a host cell is also disclosed. The enzymes are essentially pure when obtained in this manner.

Thus the present invention also discloses another method for obtaining the xylanases, i.e. expression of recombinant DNA. The present invention further describes the application of the xylanases under conditions equivalent to industrial application conditions, using high temperature and high pH.

BRIEF DESCRIPTION OF THE FIGURES

FIG. 2: Sequence alignment of- family G internal consensus sequences.

Ref=no enzyme, 715=TG456 xynD, 716=Tg53 xynD. Tensile index (A), porosity (B), tear (C) and burst (D) in relation to Schoppen-Riegler values are given.

FIGS. 5A–5D: Paper properties of paper prepared from hardwood pulp ECF bleached as described in Example 15. Ref=no enzyme, 715=TG456 xynD, 716=Tg53 xynD. Tensile index (A), porosity (B), tear (C) and burst (D) in relation to Schoppen-Riegler values are given.

FIGS. 6A–6D: Paper properties of paper prepared from softwood pulp TCF bleached as described in Example 15. Ref=no enzyme, 715=TG456 xynD, 716=Tg53 xynd. Tensile index (A), porosity (B), tear (C) and burst (D) in relation to Schoppen-Riegler values are given.

FIGS. 7A–7D: Paper properties of paper prepared from softwood pulp ECF bleached as described in Example 15. Ref no enzyme, 715=TG456 xynD, 716=Tg53 xynD. Tensile index (A), porosity (B), tear (C) and burst (D) in relation to Schoppen-Riegler values are given.

FIGS. 8A–8D: Refining curves as determined in Example 15 for TCF (A) and ECF (B) bleached hardwood pulp and for TCF (C) and ECF (D) bleached softwood pulp. Ref=no enzyme, 715=TG456 xynD, 716=Tg53 xynD.

Figure 9A:
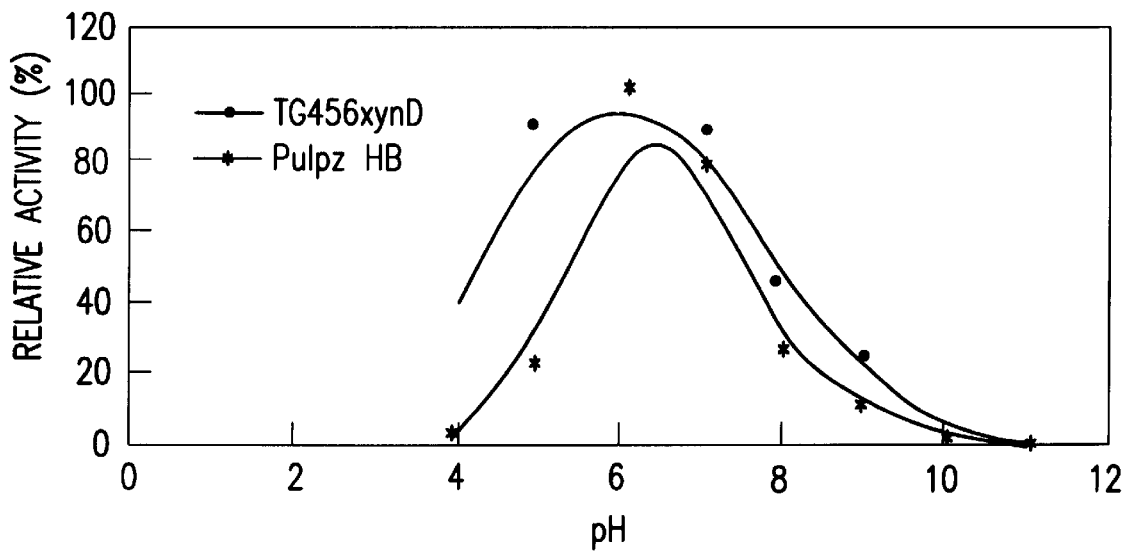
Figure 9B:
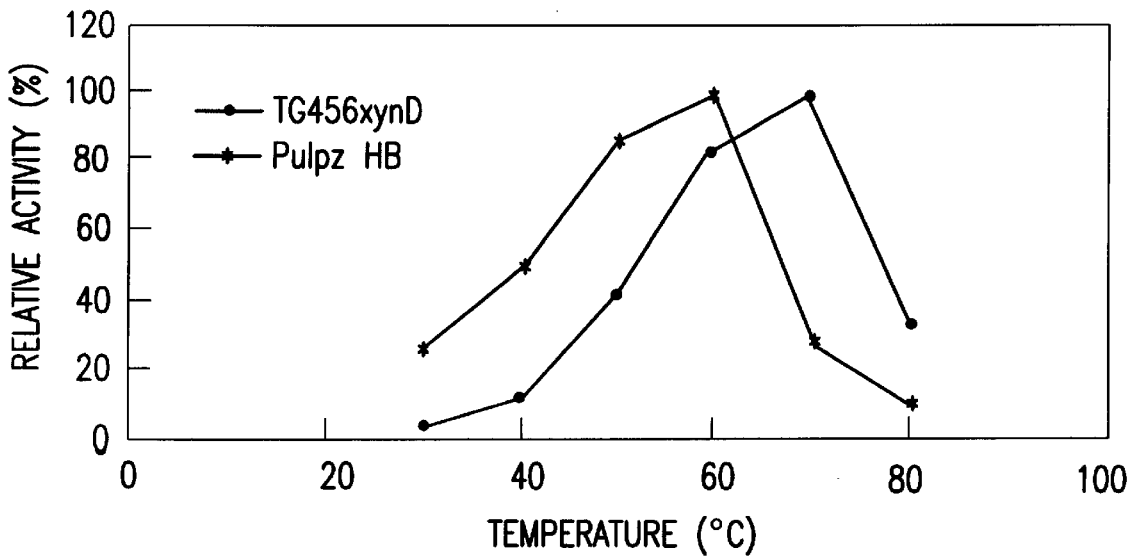

FIGS. 9A–9B: A comparison of the pH optima (A) and temperature optima (B) of the TG456 xynD xylanase and Pulpzyme HB (Novo Nordisk).

Figure 10A:
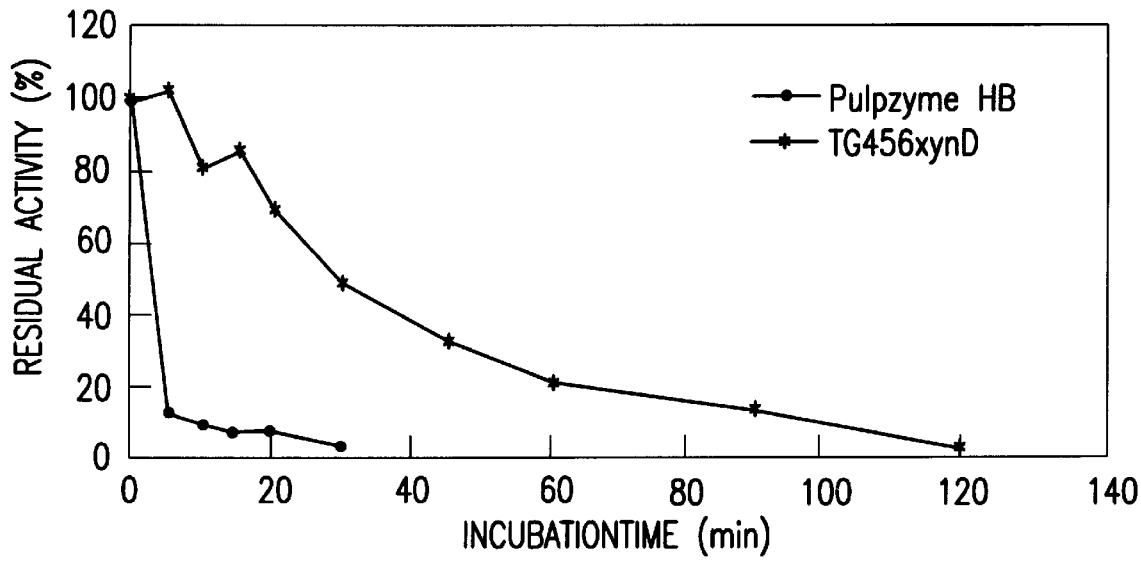
Figure 10B:
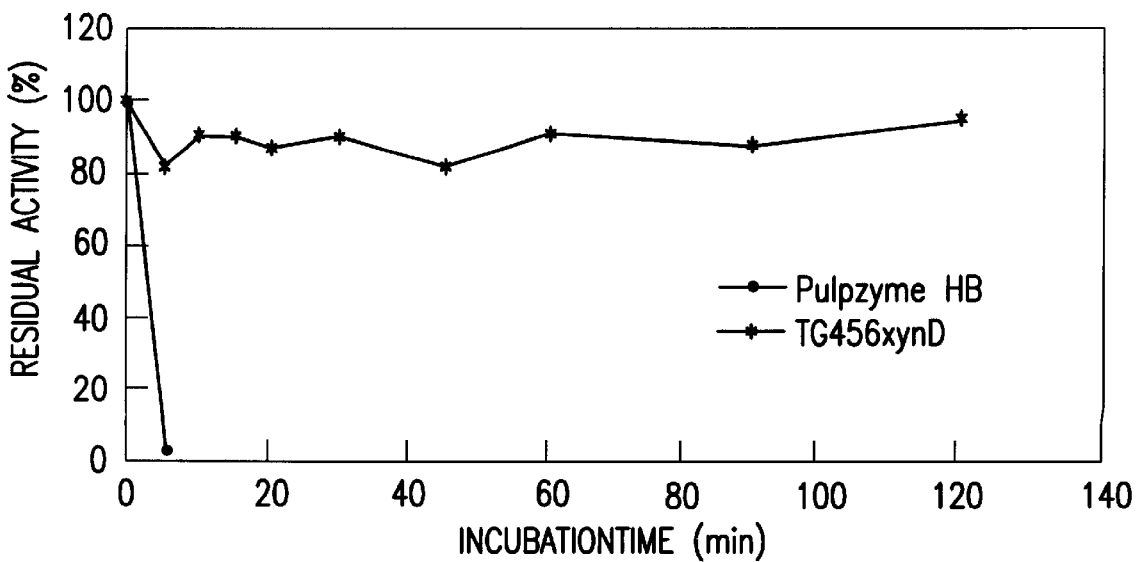

FIGS. 10A–10B: A comparison of the thermostabilities of the TG456 xynD xylanase and Pulpzyme HB (Novo Nordisk) at 80° C., pH 7.0 (A) and at 65° C.; pH 9.0 (B).

DETAILED DESCRIPTION OF THE INVENTION

The present invention discloses microorganisms which have been isolated from hot springs in New Zealand. These microorganisms have been characterized as anaerobic thermophilic bacteria and have been classified according to Rainey (1992. PhD thesis, University of Waikato, Hamilton, New Zealand).

The microorganisms have subsequently been screened using a xylan-agar diffusion assay. Strains which showed a clearing zone in this test were selected as potential xylanase producing strains. The strains were grown under anaerobic conditions at pH 7-0 and T=75 or 80° C. depending on the organism. After concentration by ultrafiltration, the culture broth was analyzed for xylanase activity in an assay at pH=6.5 and 9 and T=80° C. (Example 1).

Six different strains were found to produce xylanase activity under the indicated conditions. These microorganisms have been deposited at the CBS (Centraalbureau voor Schimmelcultures) on Apr. 14, 1994 under deposition numbers: CBS 211.94, CBS 212.94, CBS 213.94, CBS 214.94, CBS 215.94 and CBS 216.94 These deposits were made in conformity with the Budapest Treaty, and will become irrevocably available to the public upon the granting of the patent herein.

The present invention also discloses enzymes having xylanase activity, specifically enzymes having at least a considerable xylanase activity at a temperature of at least 80° C. and a pH of 6 or higher. Said enzymes are obtainable from the deposited strains. Said enzymes are also obtainable from mutants and variants of the deposited strains.

With the expression "considerable activity" is meant that the enzymes of the present invention have at least 80° C., at least 40% of the activity they possess at 70° C., preferably this is at least 60%, more preferably about at least 80%, even more preferably about 200%.

The present invention further describes a process for the preparation of the xylanases which are active at a temperature of about 80° C. or having a considerable activity under these conditions. The process comprises cultivation of the deposited microorganisms of the present invention in a suitable medium, followed by recovery of the enzymes having the indicated activity. Isolation and purification of the xylanase can be performed using standard procedures known in the art.

A partial purification of the enzymes is exemplified in Example 2. In this example the cells are first removed by hollow fibre filtration. Subsequently, the protein is further purified by ammonium sulphate addition to a final concentration of 1M. The solution is then brought on a phenyl sepharose column and the protein eluted with 1M NaCl. Finally, the protein is concentrated by ultrafiltration and salt is removed by diafiltration.

To establish the xylan degrading potential of the xylanases at an alkaline pH, a comparison of the activities of the xylanases isolated from the indicated strains at a pH of 7 and 9 has been made using different substrates and a temperature of 70° C. (Example 3). The xylanases have been shown to possess considerable activity at alkaline pH. Depending on the substrate and the assay, at pH 9 the xylanases have about 20% or more of the activity they possess at pH 7. One xylanase was shown to retain 80% of its pH 7 activity at pH 9.

The thermostability of the xylanases isolated from the indicated strains varies considerably. Some of the xylanases are very thermostable they have a half-life of more than 2 hours at pH=9 and at 80° C. (see Example 4), The half-life at pH=9.0 and 80° C. of the xylanases of the invention is at least 10 minutes, preferably the half-life under these conditions is more than 20 minutes, more preferably it is more than 30 minutes, still more preferably it is more than 60 minutes and most preferably the half-life is more than 120 minutes.

The present invention also discloses the cloning and expression of a DNA sequence characterized in that it encodes a xylanase obtainable from an anaerobic thermophilic strain. The invention discloses vectors, which include expression vectors, characterized in that they contain the DNA sequence encoding the xylanases of the present invention. A microbial host cell characterized in that it is transformed with one of these vectors is also disclosed.

Sequence analysis of the DNA sequences encoding the xylanases of the invention revealed that the obtained sequences fall into two groups of enzymes families, i.e. the F-type and G-type xylanases as previously defined by Gilkes et al. (1991, Microbiol. Rev. 55: 303–315). The xynA, xynB and xynC sequences obtained from the microorganisms of the invention belong to the F-type xylanases; the xynD sequences obtained from these microorganisms belong to the G-type xylanases (see examples 6,7,8 and 9). G-type xylanases from thermophilic microorganisms have not been described previously to the best of our knowledge. The thermophilic microorganisms which are the source of the xylanases of the invention are herein defined as microorganisms with an optimum growth temperature which is higher than 65° C. Preferably the optimum growth temperature is higher than 68° C., more preferably the optimum growth temperature is higher than 70° C., and most preferably the optimum growth temperature is in excess of 75° C.

Expression of the both F-type and G-type xylanase DNA sequences of the invention in E.coli is shown to give an active proteins (see Example 10 and 11). Said proteins are active at a temperature of 80° C.

The cloning and expression demonstrated in the examples of the present description makes possible expression of the genes in homologous organisms. Expression can also be performed in other microorganism using suitable expression and secretion regulating sequences. Organisms of choice are yeast, fungi and bacteria. Specific micro-organisms include strains selected from *Aspergillus niaer, Kluyveromyces lactis* and *Bacillus licheniformis*.

The enzymes of the present invention have been shown to possess a considerable activity on oat spelts xylan and on birchwood xylan.

The enzymes of the present invention have further been tested for their bleaching capacity. This bleaching capacity is determined by the delignifying activity of the enzymes of the present invention. The invention discloses enzymes which have a significant delignifying activity, as measured on several wood pulps. The enzyme preparations, xylanases, are capable of delignifying wood pulp at a temperature of at least 80° C. The expression "wood pulp" is to be interpreted broadly and is intended to comprise all kinds of lignocellulosic materials.

The enzymes have been tested for their bleaching capacity on both hardwood and softwood pulps. Lignin removal has been measured according to two different methods (Example 5). Lignin in the medium was determined by the A300 test. In this test all preparations showed significant delignifying activity at 80° C. on both hard- and softwood. At pH 9 and 80° C. the activity on softwood was at leas. 43% of the activity at pH 6, while on hardwood 3 strains showed at pH 9 activities of more than 50% as compared to pH 6, and 3 others 18–30%. Bleaching of softwood pulp was also measured by determining the decrease in the lignin content of the pulp using the kappa test. The kappa number was decreased 0.5 to 14 units after incubation of the pulp at pH 9 and 80° C. with the xylanase preparations.

Additionally, the bleaching capacity of the enzymes of the present invention can be measured by e.g. the increase of ISO brightness of paper produced with conventionally treated pulp, additionally incubated with said enzymes, as compared to incubation without enzymes. Said conventional treatment comprises exposition to bleaching agents such as $H_2O_2$, ozone, $Cl_2$ or $ClO_2$, according to the art.

The cloned F-type and G-type xylanases of the invention as expressed in *E.coli* have also been tested for their performance in ECF bleaching experiments on both softwood and hardwood pulp (see Example 12). Surprisingly, we have observed that the G-type xylanases (encoded by the xynD genes) show a much better performance in bleaching sequences on both softwood and hardwood pulp as compared to the F-type xylanases, up to 6.8% ISO delta brightness over the no-enzyme control, which compares to at most 1.2% ISO brightness increase for the best F-type xylanase. Further testing of the thermostable G-type xylanases showed that they also produce excellent results in TCF bleaching experiments on both softwood and hardwood pulp (see Examples 14 and 15). Verification of the properties of the paper produced from the thus bleached pulp showed no significant differences with the no-enzyme control paper.

The cloned G-type xylanases are highly thermostable, even at high pH. A half-life at 80° C. and pH 7.0 of more than 30 minutes was measured. At 65° C. and pH 9.0 the half-life of the enzyme is not significantly reduced, even after 120 minutes of incubation (see Example 16). The half-life at pH 9.0 and 65° C. of the G-type xylanases of the invention is at least 10 minutes, preferably the half-life under these conditions is more than 20 minutes, more preferably it is more than 30 minutes, still more preferably it is more than 60 minutes and most preferably the half-life is more than 120 minutes.

The invention discloses DNA sequences encoding thermostable G-type xylanases the internal consensus fragment (ICF) of which shows more than 80% identity with the ICF of SEQ ID NO 12. The G-type ICF is herein defined as the fragment which lies in between the sequences corresponding to SEQ ID NO 4 and SEQ ID NO 5 in SEC ID NO 12 (nucleotide positions 295 to 623). Preferably the identity with the G-type ICF is more than 87%, more preferably the identity is more than 95%, most preferably, the identity is more than 99%.

In a further embodiment, the invention discloses G-type xylanase sequences which share at least 70% identity with the amino acid sequence of SEQ ID NO 13. Preferably this amino acid identity is-more than 80%: more preferably, the amino acid identity is more than 90%; still more-preferably the amino acid identity is more than 95%; most preferably the amino acid identity is more than 99%.

The enzymes of the present invention can be used immediately after the oxygen delignification step in the pulp preparation process described above. As a consequence of the temperature and pH characteristics of the enzymes, extensive cooling and pH adaptation can be avoided. In another embodiment of the invention, the enzymes are used before or during the oxygen delignification step. Before this step the lignin concentration is much higher and therefore the effect of the application of the xylanase is much larger.

Furthermore, applications of the enzyme preparations of the present invention are described, particularly a process in which wood pulp is treated with said enzyme preparations according to the invention.

Similarly, a fluff pulp can be treated with the enzyme preparations according to the invention.

The invention further relates to paper, board and fluff pulp made from a wood pulp treated with the enzyme preparations according to the invention.

EXAMPLE 1

Isolation of strains producing thermostable xylanase activity

Xylanase-producing microorganisms were obtained from hot-springs in various thermal areas of New Zealand. The strains were isolated by in situ enrichment using oat spelts xylan as substrate from hot springs having a temperature of above 70° C., and a pH between 6.0 and 8.5. Cultures of strains were obtained by further anaerobic cultivation in the laboratory on 2/1 medium plus xylan at a temperature (70°, 75° or 85° C.) corresponding to the temperature of the site from which the sample was taken.

The composition of the 211 medium plus xylan is as follows:

| Anaerobic 2/1 medium | |
|---|---|
| Resazurin (0.1%) | 1.0 ml/l |
| SL10 Trace Elements | 1.0 ml/l |
| $FeCl_3$ soln. (0.28 mg/ml) | 1.0 ml/l |
| Wolin's Vitamins | 0.1 ml/l |
| NaCl | 0.9 g/l |
| $MgCl_2.6H_2O$ | 0.2 g/l |
| $K_2HPO_4$ | 1.5 g/l |
| $KH_2PO_4$ | 0.75 g/ |

-continued

| | |
|---|---|
| NH$_4$Cl | 0.9 g/l |
| Cysteine | 0.75 g/l |
| Yeast Extract | 0.5 g/l |
| Bacto Tryptone | 1.0 g/l |
| Oat spelts xyian | 2 g/l |
| pH 7.0 | |
| | |
| Dispense under N$_2$ gas | |
| Wolin's Vitamin Mixture | mg/100 ml |
| | |
| Biotin | 2.0 |
| Folic acid | 2.0 |
| Pyridoxine HCl | 10.0 |
| Riboflavin | 5.0 |
| Thiamine | 5.0 |
| Nicotinic acid | 5.0 |
| Pantothenic acid | 5.0 |
| Vitamin B12 | 0.1 |
| p-Aminobenzoic acid | 5.0 |
| Thioctic acid | 5.0 |
| SL10 Trace Elements modified | |
| | |
| 5M HCL | 15 ml |
| | mg/l |
| | |
| ZnCl$_2$ | 70 |
| MnCl$_2$.4H$_2$O | 100 |
| H$_3$BO$_3$ | 6 |
| CoCl$_2$.6H$_2$O | 130 |
| CuCl$_2$.2H$_2$O | 2 |
| NiCl$_2$.2H$_2$O | 24 |
| NaMoO$_4$. 2H$_2$O | 36 |

Pure cultures of strains were obtained from single colonies in agar roll tubes. Culture concentrates obtained by ultrafiltration were tested for xylanase activity at 70° and 80° C. and, at pH 6.5 and 9.0 using a dyed xylan method (see below) and the PAHBAH method (see Example 3).

Six strains which were deposited at the CBS (Centraal Bureau voor Schimmelcultures) are depicted in Table 1.

TABLE 1 deposition numbers of strains used in this patent application

| strain | CBS accession number |
|---|---|
| TG 53 | CBS 211.94 |
| TG 453 | CBS 212.94 |
| TG 456 | CBS 213.94 |
| TG 457 | CBS 214.94 |
| TG 479 | CBS 215.94 |
| TG 631 | CBS 216.94 |

Dyed xylan, composed of larchwood xylan coupled to Remazol Brilliant Blue R (Sigma), was prepared following a method described by Biely et al (1985) Anal. Biochem 144, 142–146. Larchwood xylan (6.7 g) was placed into 250 ml water and stirred for several hours at room temperature to dissolve. Remazol Brilliant Blue R (10.0 g) was added to this mixture. After dissolving, 20 ml of a Na-acetate solution (2.7 g Na-acetate in 20 ml distilled water) was added dropwise. Then a solution of 6 g NaCH in 70 ml water was added and stirring continued for 18 hours. The dyed xylan which had formed was precipitated by the addition of 700 ml 96% ethanol. After allowing to stand for 6 hours the precipitate was separated by filtration (Whatman GF/A). The filter cake was washed with 3 l of a 2:1 mixture of 96% ethanol/0.05M Na-acetate, followed by 1 l-96% ethanol and 3 l acetone until the filtrate was colorless. The yield was 10.5 g dyed xylan.

For the enzyme assay, 5.1 g dyed xylan was dissolved in 150 ml 0.1M MOPS buffer, pH 6.8. The mixture was stirred at 70° C. for 4 hours to dissolve. After cooling to room temperature insoluble material was removed by centrifugation at 10,000 x g. For activity assays, the stock solution containing 3.34% w/v dyed xylan was diluted with 0.1M MOPS buffer, pH 6.8 to give a 0.5% dyed xylan working solution.

The enzyme assay using dyed xylan was performed by adding 0.9 ml dyed xylan solution (0.5%) to 0.6. ml enzyme preparation in an appropriate buffer with mixing. A portion (0.4 ml) of this mixture was transferred into 0.8 ml 96% ethanol as control (blank). The remaining solution was incubated at 70° C. for 90 minutes. The reaction was terminated by transferring 0.4 ml of the test mixture into 0.8 ml 96% ethanol. This solution was left at room temperature for 30 minutes to allow for the precipitation of uncleaved dyed xylan. The test samples were centrifuged at for 5 minutes at full speed in a Beckman Microfuge E, and the absorbance of the supernatant was measured at 595 nm in a spectrophotometer.

EXAMPLE 2

Isolation of enzyme preparations

Anaerobic fermentations were carried out in 2 l Schott bottles containing 1800 ml of 2/1 plus xylan medium in stationary incubation at a temperature of either 75 or 80° C. (depending on the organism being cultured) for 24 hrs. From 10 l of well-grown culture the cells were removed by hollow fibre filtration in the presence of 0.01% triton X100 (Amicon DC 10 LA and Amicon 0.1 μm H5MP01-43 filter). Ammonium sulphate was added to the cell free culture medium to a final concentration of 1M. The resulting solution was pumped onto a 9×15 cm column containing 1 l of phenyl sepharose (Pharmacia-Fast Flow-low substitution) equilibrated with 1M ammonium sulphate. The flow rate was 150–200 ml/minute. The column was washed with 5 l 1M ammonium sulphate. The xylanase was eluted with 5 l 1M NaCl. Fractions were collected in 500–1000 ml volumes. The xylanase activity was determined (with the PAHBAH method as described in Example 3) in the fractions and the active fractions were pooled, ultrafiltered to a small volume and diafiltered to reduce the salt concentration using an Amicon Stirred Cell (Model 2000A or 8400) with an YM2 membrane.

EXAMPLE 3

Characterization of xylanase activities of the partially purified enzyme preparations Analytical methods Assays for xylanase activity were performed using modified procedures of the Sumner assay (Sumner et al. 1921. J. Biol. Chem. 47: 5–9). Alternatively xylanase activity was determined using a modified PAHBAH assay, based on a method from Lever (1973. Biol. Med. 1: 274–281).

Procedure 1

Sumner assay of xylanase activity on oat spelts xylan

An oat spelts xylan substrate solution is prepared as follows: 4 g oat spelts xylan is suspended in 100 ml demineralized water. The suspension is sonicated for 6 minutes (sonicator: Sonics & Materials, Vibracell type VC 250 B), incubated at 100° C. for 10 min., and centrifuged for 10 min. at 10,000 rpm in a Sorvall RC-5B centrifuge. The supernatant is used as a substrate solution and contains about 2% oat spelts xylan.

The assay is carried out as follows: A test tube is filled with 200 μl oat spelts xylan solution, 600 μl aliquots of enzyme preparation (Example 2) diluted in the appropriate buffer. The test tube is incubated under measuring conditions in a waterbath for 15 minutes. After the incubation, 7.2 ml DNS (dinitrosalicylic acid) reagent is added. The mixture is heated in a waterbath at 100° C. for 10 minutes, whereafter the test tube is cooled on ice. The absorbance is measured at 575 nm. To eliminate the background absorbance of the enzyme samples a control experiment is executed as follows: a tube containing substrate without enzyme preparation is incubated under the same conditions as the test samples. After the 15 minutes incubation 7.2. ml. DNS and the enzyme sample is added (in this order).

One unit of xylanase (xU) activity is defined as the amount of enzyme producing 1 μmol of xylose-equivalent, .measured as reducing-sugar.

Actual measuring conditions were pH 7.0,. 9.0 and 70° C. At pH-7 a 50 mM phosphate buffer was used, and at pH 9 a 50 mN borate/KOH buffer.

TABLE 2 relative xyllanase activities on oat spelts xylan, measured at 70° C.

| Strain | Activity (%) | |
|---|---|---|
| | pH 7.0 | pH 9.0 |
| TG 453 | 100 | 57 |
| TG 456 | 100 | 39 |
| TG 457 | 100 | 31 |
| TG 479 | 100 | 19 |
| TG 631 | 100 | 31 |

Procedure 2

Sumner assay of xylanase activity on Birchwood xylan

Essentially the same method as described in procedure 1 is used. Instead of an oat spelts xylan solution a birchwood xylan suspension is used. A birchwood xylan substrate solution is prepared as follows: 4 g birchwood xylan is suspended in 50 ml 0.2N NaOH and agitated until visibly dissolved. The pH of the solution is adjusted to 7.0 with glacial acetic acid, water is added to 100 ml and the solution is centrifuged at 10,000 rpm in a Sorvall RC-5B centrifuge. The supernatant is used as a substrate solution and contains about 3% birchwood xylan. The test conditions were pH 7 and 9 and 70° C. The results are shown in Table 3.

TABLE 3 relative xylanase activities on birchwood xylan, measured at 70° C.

| Strain | Activity (%) | |
|---|---|---|
| | pH 7.0 | pH 9.0 |
| TG 453 | 100 | 40 |
| TG 456 | 100 | 20 |
| TG 457 | 100 | 21 |
| TG 479 | 100 | 12 |
| TG 631 | 100 | 21 |

Procedure 3

PAHBAH assay of xylanase activity on oat spelts xylan

The modification of the PAHBAH method (Lever, 1973) is to the PAHBAH reagent, as follows: 0.05M trisodium citrate, 0.1M $Na_2SO_3$, 0.02M $CaCl_2$, 0.5M NaOH and 0.1M p-hydroxybenzoic acid hydrazide (PAHBAH).

For the assay of the enzyme preparations 0.05 ml or 0.1 ml of enzyme preparation is mixed with 0.3 ml substrate buffer (50 mM Bis-Tris-Propane, pH as required, +0.2% oat spelts xylan in suspension). An appropriate amount of water is added to a final volume of 0.5 ml. Incubation is usually made at 70° C. for 30 min. To stop the reaction, 1.0 ml of PAHBAH reagent is added after incubation and the samples are heated at 100° C. for 6 minutes. The blanks consist of substrate buffer incubated identically to the sample to which the enzyme is added after the PAHBAH reagent. Before determination of the absorption at 420 nm, all samples are centrifuged 1 min at full speed in a Beckman Microfuge E to remove suspended xylan from the supernatant. The results are shown in Table 4. From this Table it can be concluded that at pH 9.0, 80° C. all strains still have a considerable activity as compared with pH 6.0, 70° C.

TABLE 4 relative xylanase activities on oat spelts xylan, measured with the PAHBAH assay

| Strain | Activity (%) | |
|---|---|---|
| | pH 6.0, 70° C. | pH 9.0, 80° C. |
| TG 53 | 100 | 57 |
| TG 453 | 100 | 20 |
| TG 456 | 100 | 65 |
| TG 457 | 100 | 82 |
| TG 479 | 100 | 30 |
| TG 631 | 100 | 65 |

EXAMPLE 4

Thermostability of xylanase activities

The half-life of the xylanase activity of the enzyme preparations was determined as follows. The enzyme preparation was diluted 1/10 in 100 mM TAPS buffer (pH 9.0 at 80° C.) and incubated at 80° C. A sample was removed at 0, 10, 20, 40, 60 and 120 minutes and added to 100 mM MOPS buffer (pH 6.0 at 70° C.) on ice, to a final dilution of 1/20 to 1/100 as appropriate for the final assay. The samples were kept on ice until they were assayed at 70° C. and pH 6.0 using the PAHBAH assay method as described in Example 3, procedure 3. The results are shown in Table 5.

TABLE 5 thermostability of xylanase activity at pH 9.0 and 80° C., as measured with the PAHBAH assay on oat spelts xylan

| Strain | Half-life pH 9.0, 80° C. |
|---|---|
| TG 53 | 30 minutes |
| TG 453 | 60 minutes |
| TG 456 | >120 minutes |
| TG 457 | >120 minutes |
| TG 479 | <10 minutes |
| TG 631 | <20 minutes |

EXAMPLE 5

Delignification activities

Delignification capacity of the xylanases was determined with two different methods. Using the A300 method the amount of lignin released from the pulp after enzyme treatment is estimated. Using the kappa assay the remaining lignin content of pulp after treatment is measured.

Method 1: A300 test

To measure delignification with the A300 assay enzyme preparations were incubated with soft- or hardwood pulp at a concentration of 2 PAHBAH units per g of wet pulp (about 6 PAHBAH units/g of dry pulp). Incubations were performed for 2 hours at 80° C. both at pH 6.0 in MOPS buffer, and at pH 9.0 in TAPS buffer. Pulp concentration in the incubation was 0.1 g wet weight per ml. Two different types of pulp were used: Kraft softwood pulp after oxygen delignification, and Kraft hardwood pulp after oxygen delignification. Properties of these pulps are given in Table 6.

TABLE 6 properties of the pulp types used in the delignification experiments

|  | Hardwood birch | Softwood 80% spruce, 20% pine |
|---|---|---|
| Brightness, % ISO | 50.8 | 35.8 |
| Kappa number | 11.0 | 16.7 |
| Viscosity, dm$^3$/kg | 979 | 1003 |
| Calcium; ppm | 1900 | 2600 |
| Copper, ppm | 0.3 | 0.6 |
| Iron, ppm | 5.1 | 11 |
| Magnesium, ppm | 210 | 270 |
| Manganese, ppm | 25 | 70 |

The amount of lignin that was removed from the pulp was determined by measuring the absorbance of the supernatant at 300 nm, after separating the supernatant from the pulp by filtration by suction through a Whatman GF/C filter supported on a sintered glass filter. The results of the A300-test are shown in Table 7. In this assay, Delta A300 values of $\geq 0.2$ are significantly higher than background levels. Therefore, this example shows that the enzymes possess a significant delignifying activity at 80° C.

TABLE 7

A300 delignification measured at 80° C., pH 6.0 and 9.0, on soft- and hardwood

| | Delta A300 | | | | | |
|---|---|---|---|---|---|---|
| | Hardwood | | | Softwood | | |
| Strain | pH 6.0 | pH 9.0 | %* | pH 6.0 | pH 9.0 | %* |
| TG 53 | 0.7 | 0.5 | 71 | 0.6 | 0.35 | 58 |
| TG 453 | 1.0 | 0.3 | 30 | 0.7 | 0.3 | 43 |
| TG 456 | 1.0 | 0.3 | 30 | 0.6 | 0.6 | 100 |
| TG 457 | 1.0 | 0.7 | 70 | 1.0 | 0.5 | 50 |
| TG 479 | 0.9 | 0.16 | 18 | 0.8 | 0.6 | 75 |
| TG 631 | 1.2 | 0.7 | 58 | 0.8 | 0.7 | 88 |

*Percentage of the activity at pH 9 as compared to pH 6

Method 2: the Kappa test

The kappa tests were performed according to TAPPI protocol T236 (available from TAPPI, Technology Park, Atlanta, USA), with some modifications. The enzyme preparation was added at a dose of 10 xU/g pulp (dry weight), and incubated for 2 hours at pH 9, 80° C. As a control pulp was incubated for the same period under the same conditions without enzyme addition. Oxygen delignified softwood pulp was used, for properties see Table 6.

The difference between the kappanumber with enzyme addition and the kappanumber without enzyme addition is called the kappa reduction, and is a value for delignification. The kappa reductions are shown in Table 8. In this assay, values of $\geq 0.5$ are significantly higher than background levels. Therefore, as in the previous example, this example shows that the enzymes possess a significant delignifying activity at 80° C.

TABLE 8 delignification as measured by kappa reduction, determined on softwood pulp, pH 9 and 80° C.

| Strain | Kappa reduction |
|---|---|
| TG 453 | 1.0 |
| TG 456 | 1.3 |
| TG 457 | 1.4 |
| TG 479 | 1.0 |
| TG 631 | 0.5 |

EXAMPLE 6

Cloning and sequence determination of internal consensus fragments of genes encoding thermostable F-type xylanases 6.1. PCR amplification of internal fragments of xylanase genes Three PCR primers were used to amplify internal consensus fragments of xylanase genes: two different forward primers (xynFA, {5' CAC ACK CTK GTK TGG CA 3', SEQ ID NO 1} and xynFB {5' CAT ACK TTK GTT TGG CA 3', SEQ ID NO 2) and one reverse primer (xynR {TMG TTK ACM ACR TCC CA, SEQ ID NO 3}). The xynFA and xynFB primers bound at the same location, but differed slightly in sequence due to slight differences in the sequence of xylanase genes at the forward consensus region. PCR conditions were as follows: (94° C. 1 minute, 50° C. 1 minute, 72° C. 1 minute)×30. All family F internal consensus fragments were approximately 350 bp.

6.2. Sequence determination of the PCR products

All internal xylanase PCR-products (ca. 350bp) were end-repaired (back-filled) as described below prior to cloning into the SmaI (phosphatased) site of the M13 mp 10 sequencing vector.

Step 1—Ammonium acetate precipitation (a) make up 50 μl PCR mixture to 100 μl with TE buffer (10 mM Tris-Cl, 1 mM EDTA, pH 8.0). (b) add 100 μl 4M CH$_3$COO-NH$_4^+$ and 250 μl 100% CH$_3$CH$_2$OH. (c) incubate on ice for 15 minutes (or overnight at −20° C.). (d). centrifuge at 16 000 rpm for 15 minutes and discard supernatant (e) wash pellet in 500 μl cold 70% CH$_3$CH$_2$OH. Re-centrifuge (16 000 rpm 5') and discard supernatant. (f) dry pellet under vacuum for 5 minutes and resuspend in 20 μl TE buffer.

Step 2—End-repair of PCR fragments (a) to 20 μl of precipitated DNA add: 3 μl 10 x Ligase buffer (Boehringer Mannheim), 1 μl 12.5 mM dNTP's (Pharmacia DNA polymerisation mixture), 0.5 μl (5U) E. coli DNA polymerase large (Kienow) fragment (BRL technologies Ltd), 0.25 μl (2.5U) T4 DNA polymerase (Boehringer Mannheim), 0.25 μl (2.5U) T4 polynucleotide kinase (Boehringer Mannheim) and H$_2$O up to 30 μl. (b) incubate at 37° C. for 30 minutes and heat-kill enzymes by incubating at 70° C. for 10 minutes.

Step 3—Gel-purification of the end-repaired xylanase fragment (a) run DNA through 2% LMP agarose in 1x Tris-acetate buffer (pH 7.8). (b) excise the 350 bp xylanase band from the agarose. (c) purify the DNA from the agarose slice using the GeneClean®) procedure (Bio101 Inc.).

Step 4—Ligation into M13mp10 (Smal-phosphatased)

(a) mix 1 μl M13mp10 vector DNA (appropriately diluted to ca. 10 ng/μl), 20–50 ng insert DNA (xylanase consensus primer fragment), 1 μl 10x ligase buffer (Boehringer Mannheim), 1 μl T4 DNA ligase (Boehringer Mannheim), and H20 up to 10 μl.

(b) incubate overnight at room temperature.

Step 5—Transformation of ligation mixture into *Escherichia coli* strain JM101:

(a) transform JM101 with the entire 10 μl ligation mixture using the DMSO-mediated transformation technique of Chung et al. (1989. Proc. Natl. Acad. Sci. 86: 2172–2175.).
(b) Plate the M13/JM101, and isolate recombinant M13 plasmids using standard procedures (Sambrook et al. 1989 Cold Spring Harbour Laboratory Press).

Recombinant M13 phage containing internal xylanase consensus fragments were sequenced from ssDNA (Sambrooket at al. 1989) on an Applied Biosystems 373A automated DNA sequencer using dye-primer chemistry (sequencing primer used was the universal M13 forward {dye-labelled} primer, ABI Ltd). All, DNA sequence data were analysed and manipulated using the G C G sequence analysis software (installed on Irix) run on a Silicon Graphics Personal Iris Workstation.

Family F xylanase internal fragment sequence results

Figure 1:
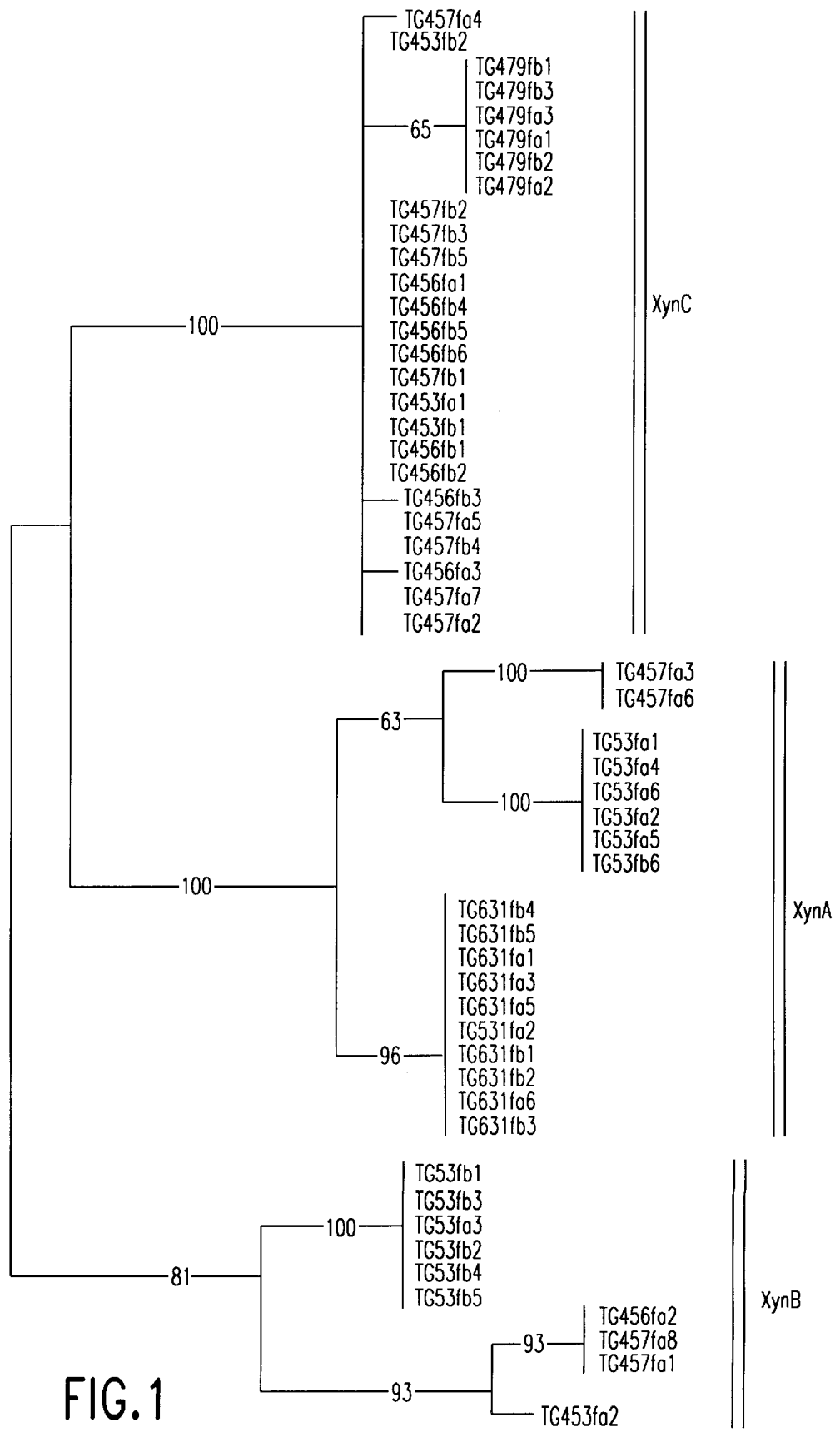
FIG. 1: Phylogenetic analysis of the internal consensus sequences of the six extremophilic strains. Sequences are named as followed; organism/forward primer/recombinant number. The branch number displayed are the values obtained from a boot-strap analysis of the sequences.

Based on the PCR fragments which were amplified from the six strains depicted in Table 1 using the xylanase consensus primers, it was predicted that each organism contained between 1 to 3 family F xylanase genes. The results have been analysed via the well known boot-strap analysis (Wisconsin Molecular Biology Package, Devereux, 1984, Nucleic. Acids Res. 12, 387–394). In FIG. 1 a dendogram of the various xylanases and strains is shown. From the nucleotide sequences of the family F consensus fragments, it now appears that each organism will contain three different family F genes. Each of the family F xylanase genes of each organism belongs to a separate xylanase cluster (based on nucleotide and primary amino acid sequence homologies), now designated as cluster A, cluster 8 and cluster C. The full-length xylanase amplified from TG 456 belongs to cluster A, and has subsequently been named TG 456 xynA. In addition, an internal consensus fragments from a TG 456 cluster B xylanase (TG 456 xynB) and a cluster C xylanase (TG 456 xync) have been identified.

EXAMPLE 7

Cloning and sequence determination of internal consensus fragments of genes encoding thermostable G-type xylanases 7.1 PCR amplification of internal fragments of G-type xylanase genes The Family G internal consensus fragments (ICFs) were isolated with the Polymerase Chain Reaction (PCR), using the forward and reverse family G consensus primers (GF and GR). The PCR profile was as follows:
n.b. °C. refers to degrees celsius.
refers to the number of cycles (i.e. x1 equals ONE cycle)
(94° C., 4 minutes) x 1
(94° C., 1 minute;. 45° C., 1 minute; 72° C., 1 minute) x 35
(94° C., 1 minute;
45° C., 1 minute; 72° C., 6 minute) x 1

The PCRs were performed in 50 uL reactions using the following ingredients: 100 ng GF primer; 100 ng GR primer; 0.25 mM dNTPs; 1 Unit Taq Polymerase; 0.25 mM MgCl2; 10 mM Tris-HCl, pH 8.8; 50 mM KCl; 0.001% Gelatin; 1–10 ng template DNA.

Two PCR primers were used to amplify consensus fragments of xylanase genes:
GF: TATNTGRSTNTMTATGGWTGG (forward internal consensus primer) SEQ ID NO 4.
GR: CCGCTNCTTTGGTANCCTTC (reverse internal consensus primer) SEQ ID NO 5.

With all six strains a PCR fragment was found upon amplification with the consensus primers.

Two species of PCR-products (DNA fragments) were amplified: a 300 bp fragment of the expected size, plus an unexpected 600 bp PCR-product this 600 bp fragment was a head-to-tail dimer of the 300 bp PCR-product; presumably this 600 bp species was a result of self-priming during the PCR reactions, as a consequence of homology between the Gr and GR primers.

7.2 Sequence determination of the PCR products

The 300 bp fragments amplified from each organism were end-repaired (see example 6).

The end-repaired fragments were then purified from a 1% low melting temperature agarose gel (run in Tris-acetate running buffer) using the Geneclean (Bio 101, La Jolla, Calif.) procedure.

Approximately 10 ng of the end-repaired and gel-purified 300 ICFs were ligated into the Smal site of M13mp10 using BM T4 DNA ligase, in 10 uL reactions.

7.3 Sequence determination of the PCR products

Six independent phages originating from strains TG457 and TG53 were sequenced. It appears from the alignments (FIG. 2) that only a single G-type xylanase gene is present in each of these strains. In addition M13 mp 10 recombinants containing family G ICFs from TG453, TG456, TG479 and TG631 were sequenced. These organisms contained all a family G xylanase gene encoding an essentially identical xylanase, although variations in the DNA sequence are up to 13%.

EXAMPLE 8

Sequence of full-length F-type xylanases

On the basis of the internal PCR fragments 3 different type of F-xylanase genes have been identified: xynA, xynB and xynC. Using Genome Walking PCR (GWPRCR) full length xylanase genes have been isolated from most of the strains.

Full length sequences of the TG456 xynA gene have been determined. The complete sequence of the xyna gene is given in SEQ ID NO 6. The encoded amino acid sequence of the TG456 xylanase A is provided in SEQ ID NO 7.

For xynS and xynC it was discovered that the genes encode multi-domain enzymes, with one xylanase domain. These xylanase domains have been subcloned using PCR primers designed on sequences at the border of the xylanase domain.

The partial sequence information for the xynB and xynC genes originating from TG456 are given in SEQ ID NO 8 and SEQ ID NO 10, respectively. The encoded amino acid sequences of the TG456 xylanases B and C are given in SEQ ID NO 9 and SEQ ID NO 11, respectively.

EXAMPLE 9

Complete sequence of G-type xylanase genes

Using Genome Walking PCR (GWPRCR) the full length xynd genes have been isolated from most of the strains.

The complete sequence for the xynD gene of TG456 is given in SEQ ID NO 12 and the encoded TG456 xylanase D amino acid sequence is provided in SEQ ID NO 13.

EXAMPLE 10

Construction of expression vectors and hosts for xylanase production from cloned genes In the consensus PCR primers appropriate restriction sites have been designed, which allow the subcloning of xylanase genes in suitable expression vectors.

The xynA and xynC genes are inserted NcoI-BamHI into the pJLA602 expression vector [Schauder, B., Blucker, H., Frank, R., and McCarthy, J. E. G. (1987). Inducible Expression Vectors Incorporating the *Escherichia coli* atpE Transcriptional Initiation Region. Gene 52: 279–283.]) for in-frame fusion with the lambda L and R promoters [Gibbs, M. G, Saul D. J, Luthi, E., and Bergquist, P. L. (1992). The beta-mannanase from "Caldocellum saccharolyticum" is Part of a Multidomain Enzyme. Appl. Environ. Microbiol. 58 (12): 3864–3867.]

XynB and xynD genes were inserted into the unique SphI-BamHI sites of pJLA602.

Constructs were transferred into the hosts *E.coli* JM101 and *E.coli* DH5α using standard transformation techniques.

Figure 3B:
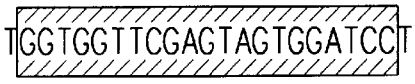
FIG. 3: The xylanase domain of xynD from-TG456 inserted as a SphI-BamHI fragment in pJLA602.
Figure 4A:
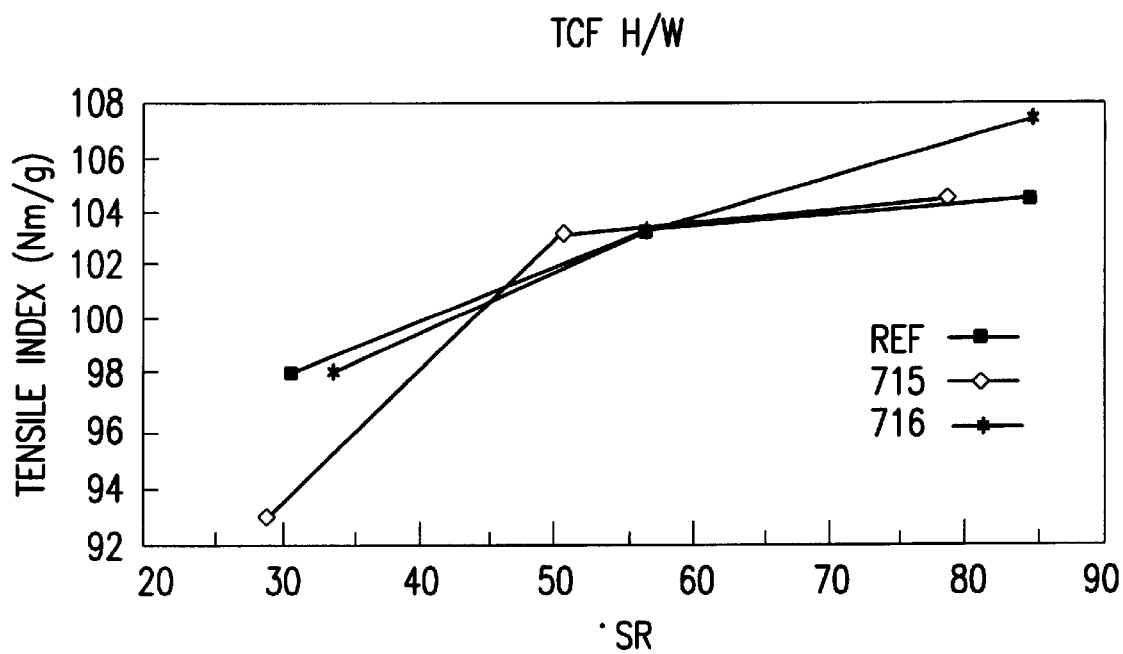
FIGS. 4A–4D: Paper properties of paper prepared from hardwood pulp TCF bleached as described in Example 15.
Figure 4B:
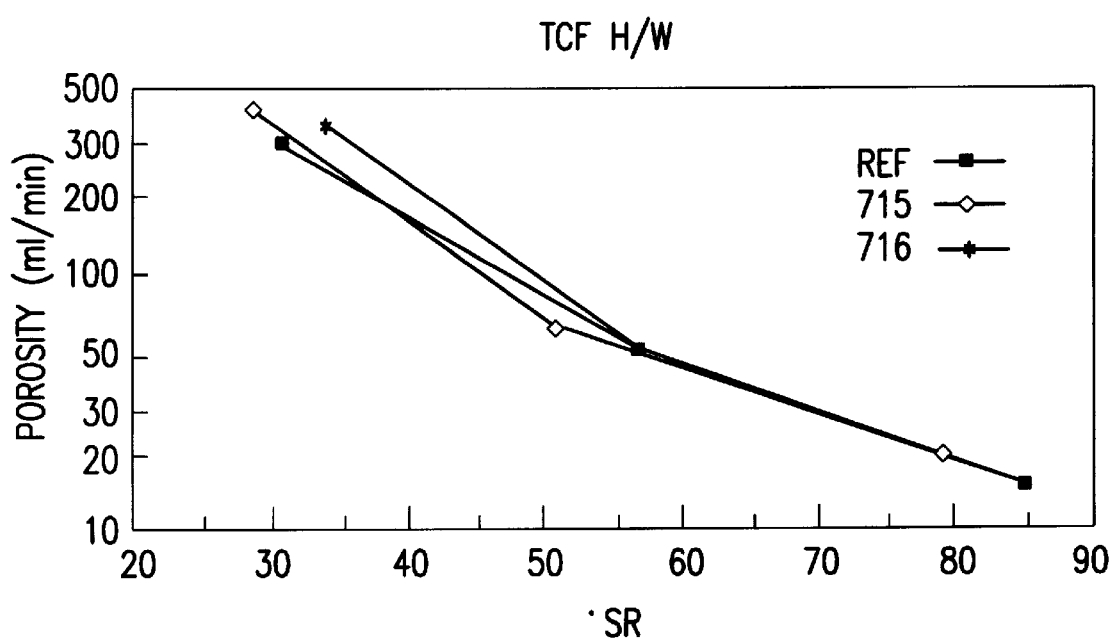
Figure 4C:
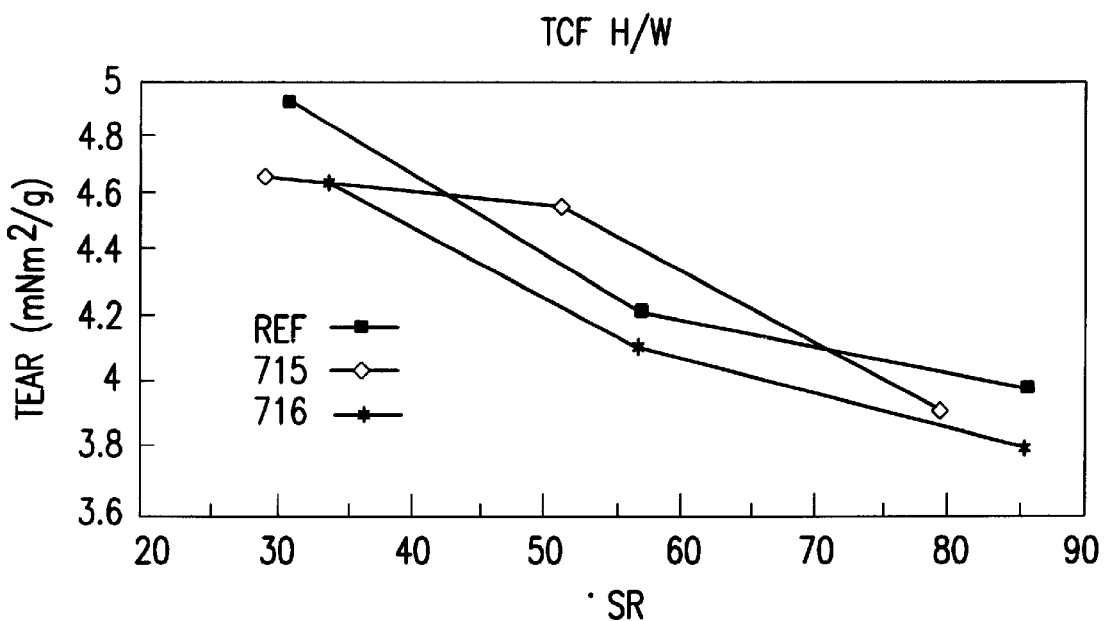
Figure 4D:
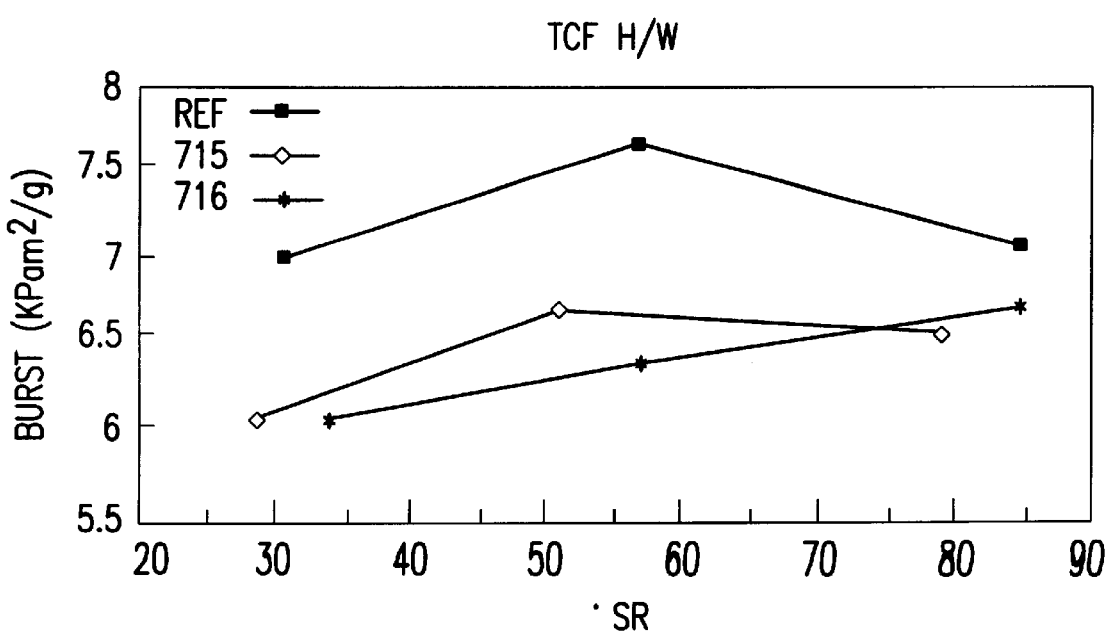
Figure 5A:
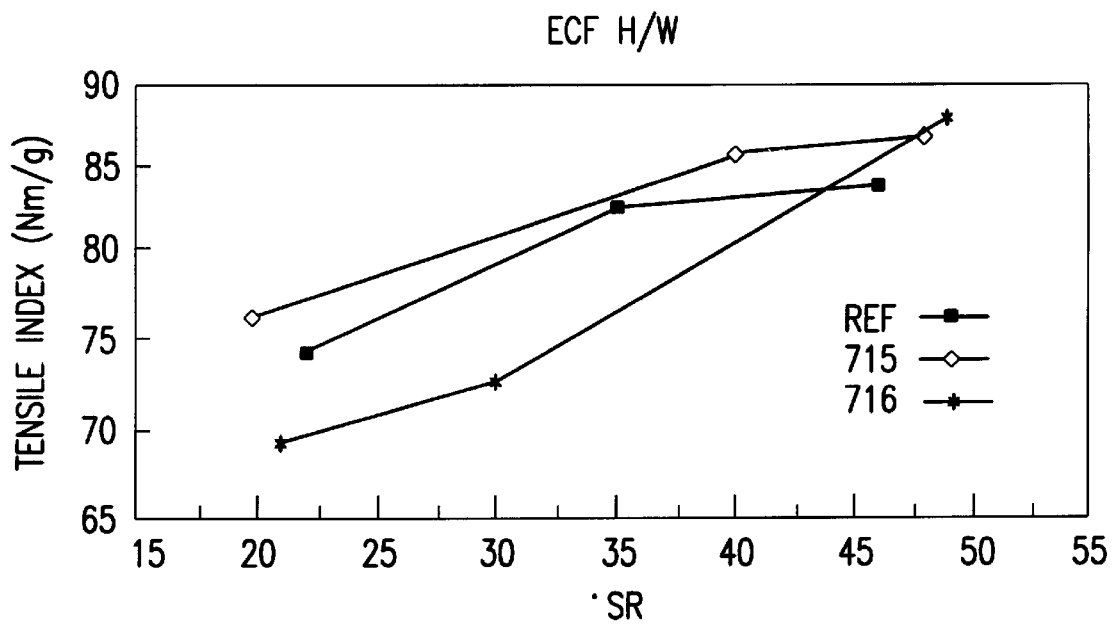
Figure 5B:
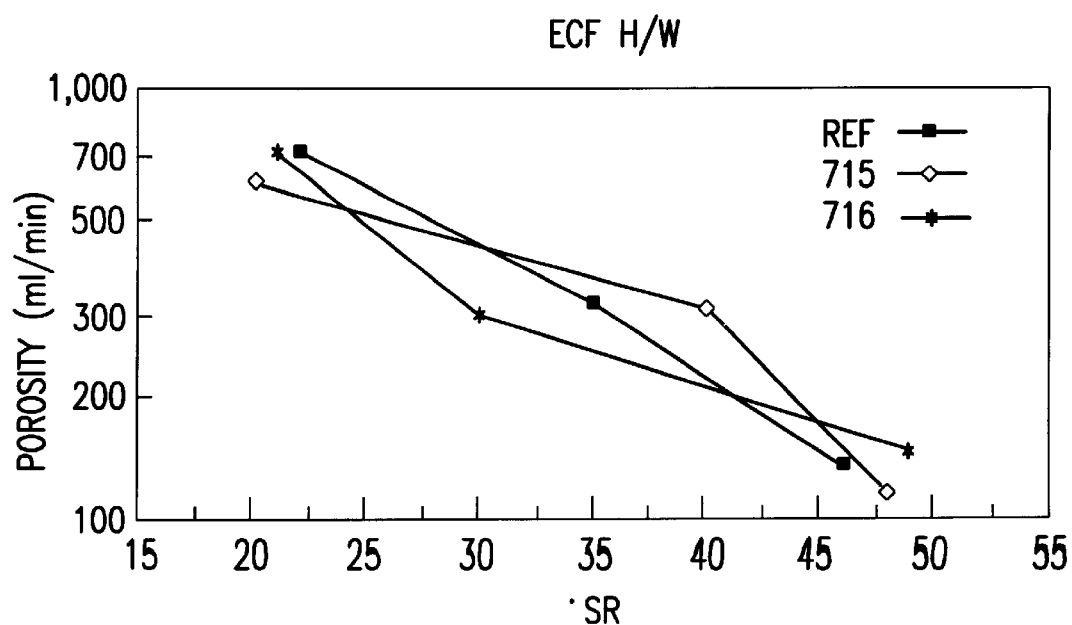
Figure 5C:
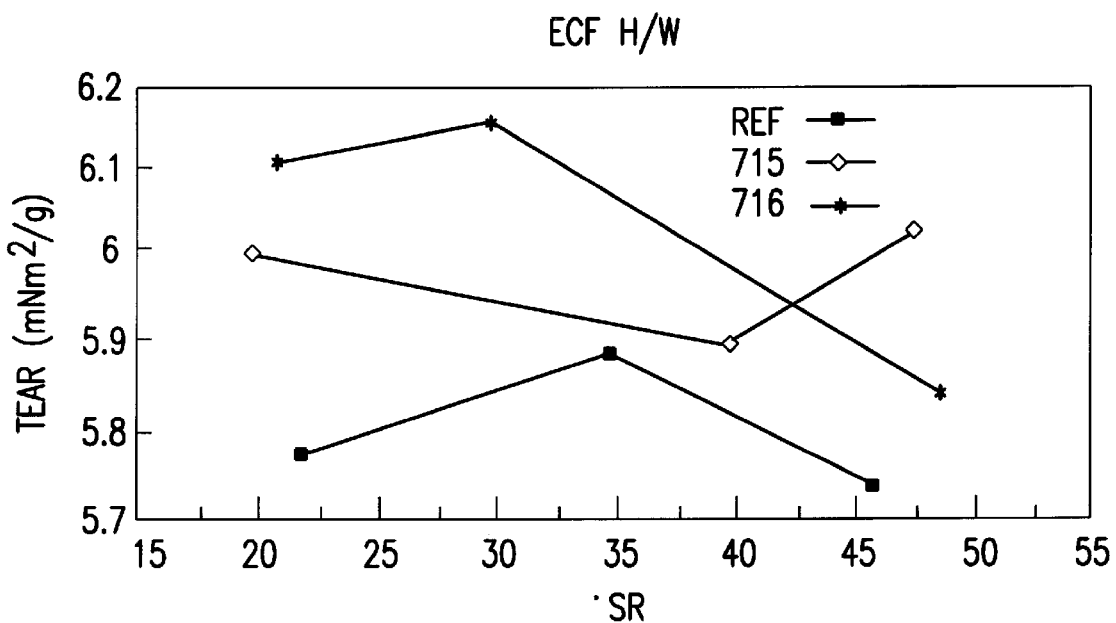
Figure 5D:
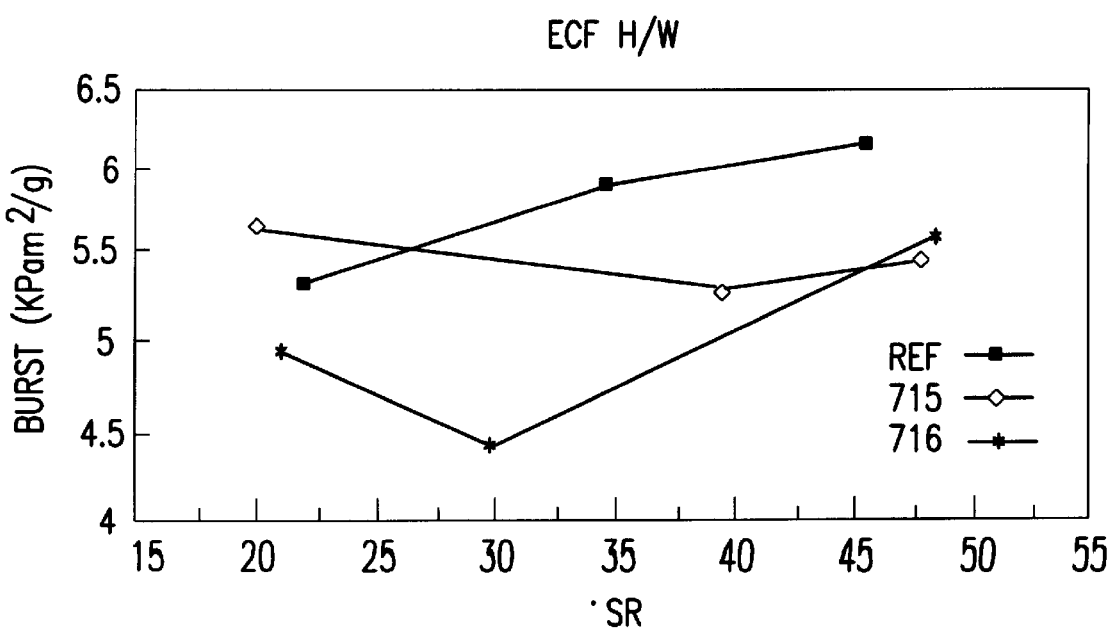
Figure 6A:
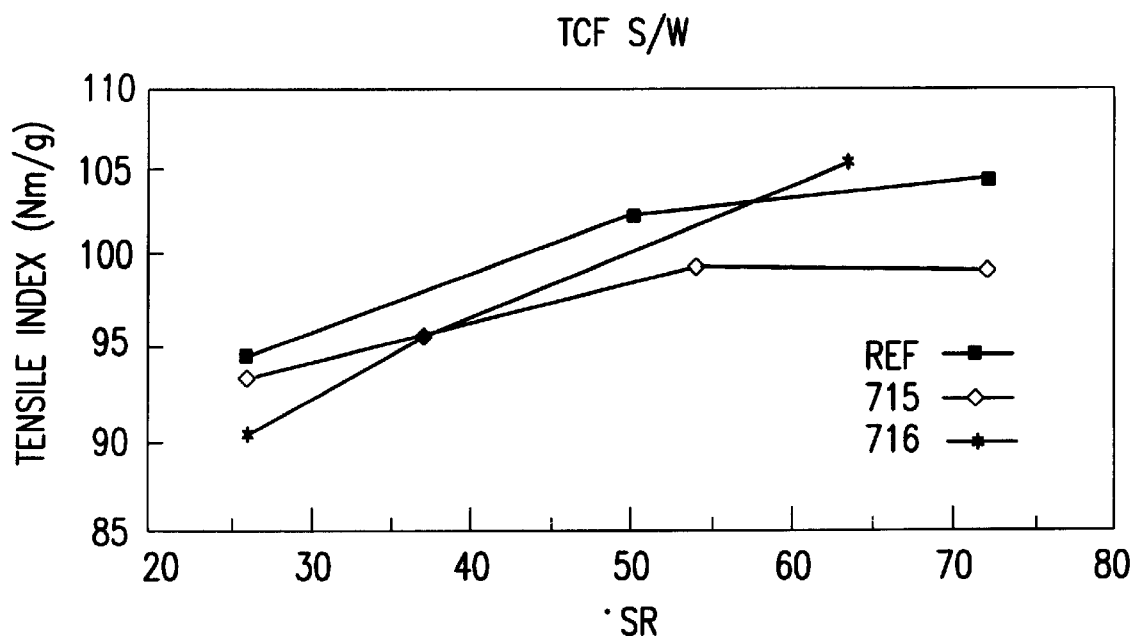
Figure 6B:
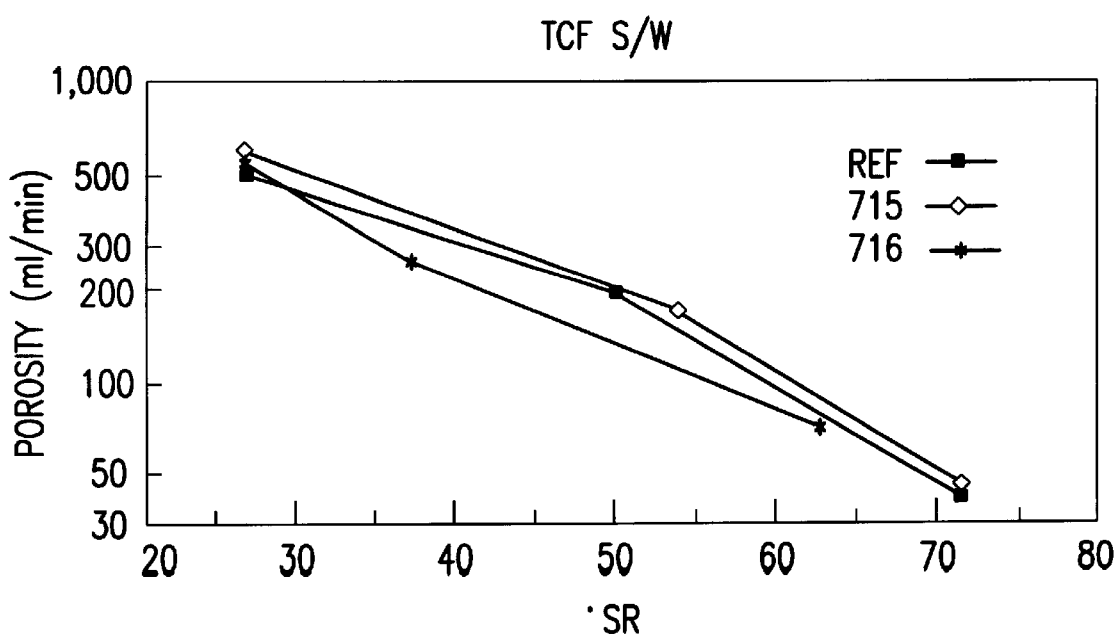
Figure 6C:
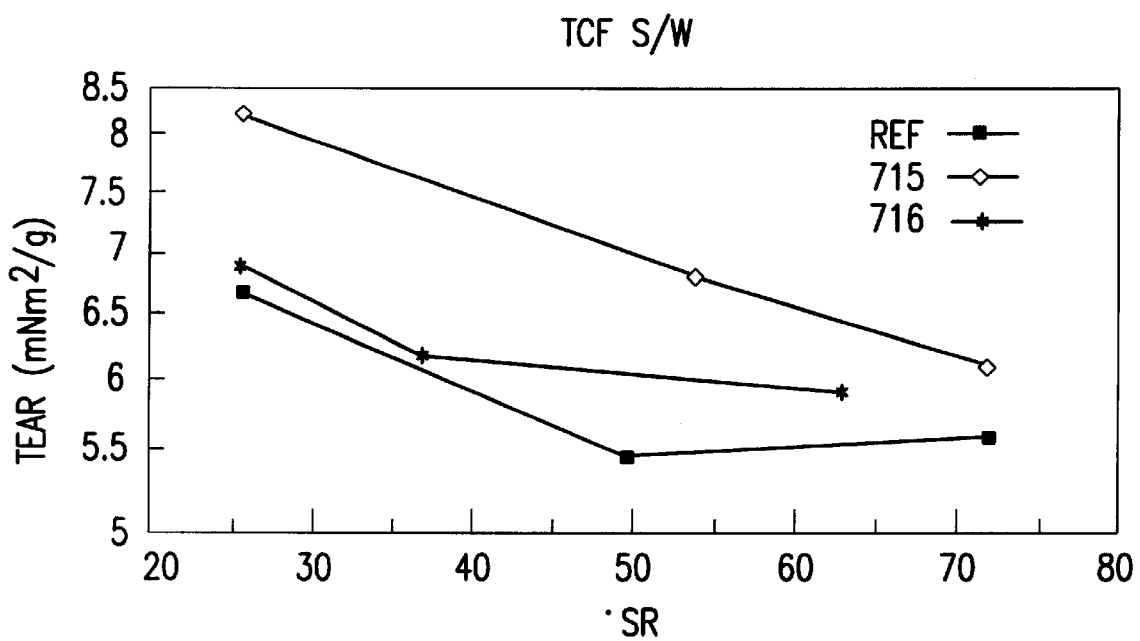
Figure 6D:
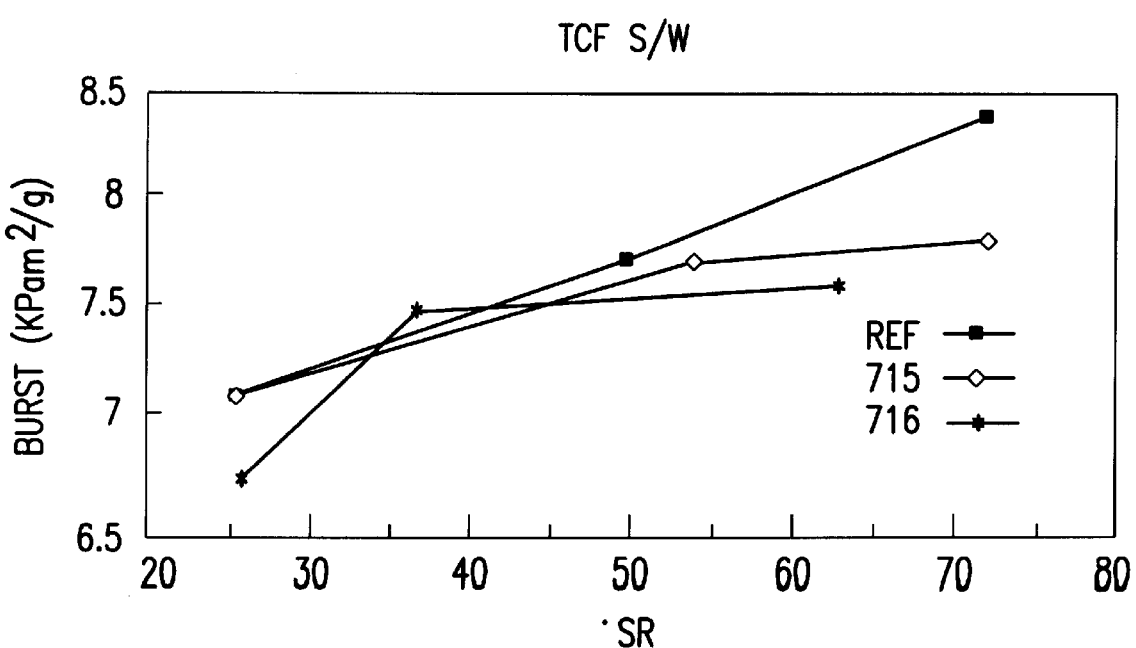
Figure 7A:
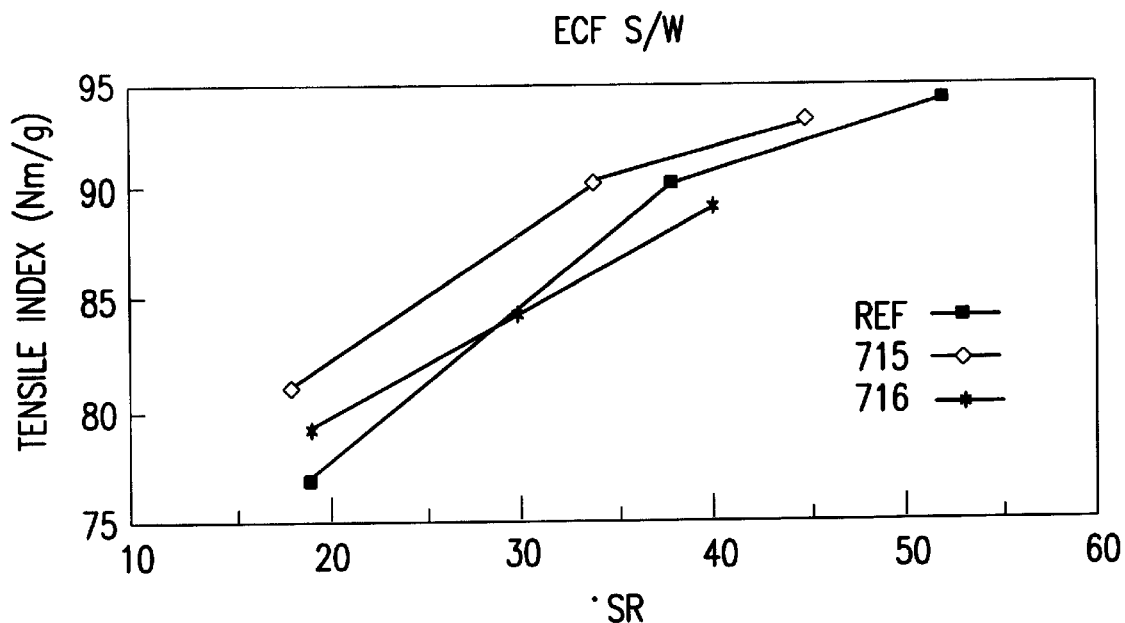
Figure 7B:
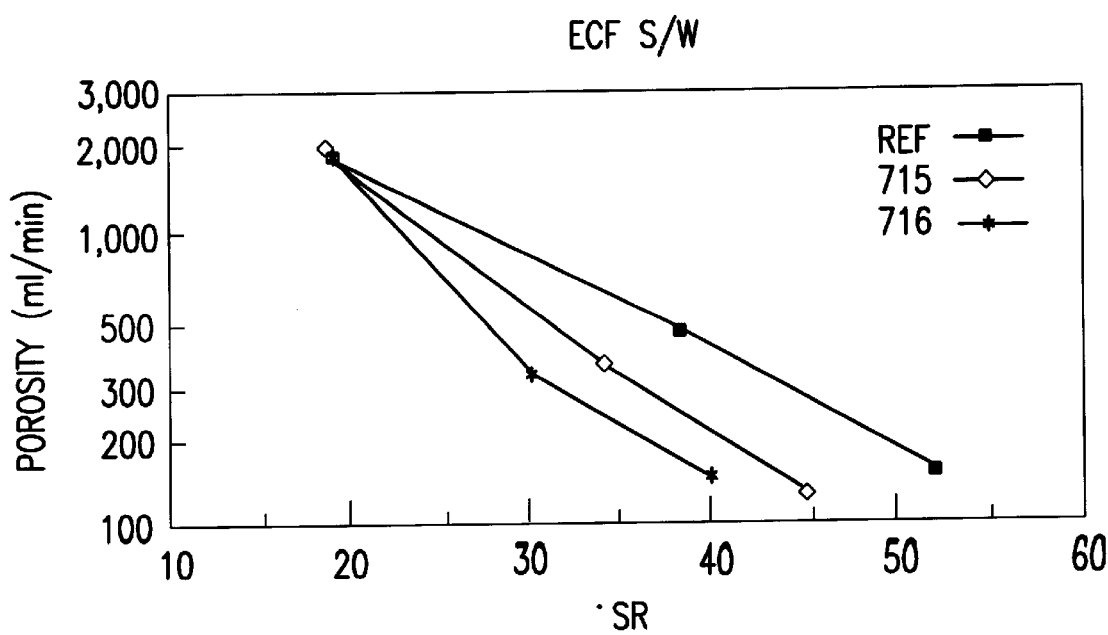
Figure 7C:
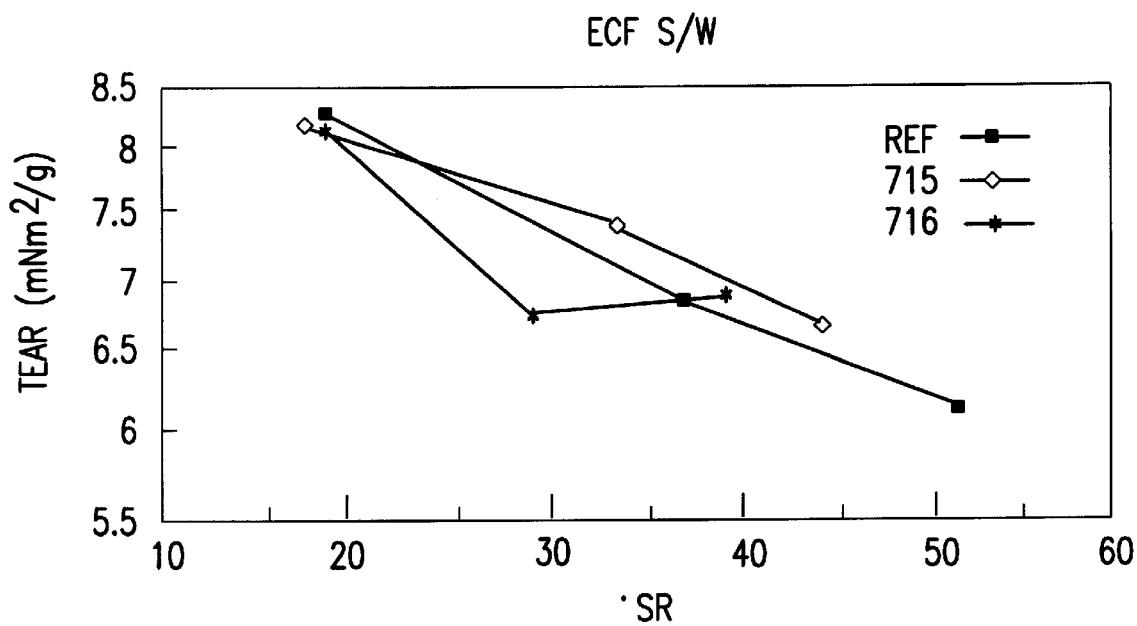
Figure 7D:
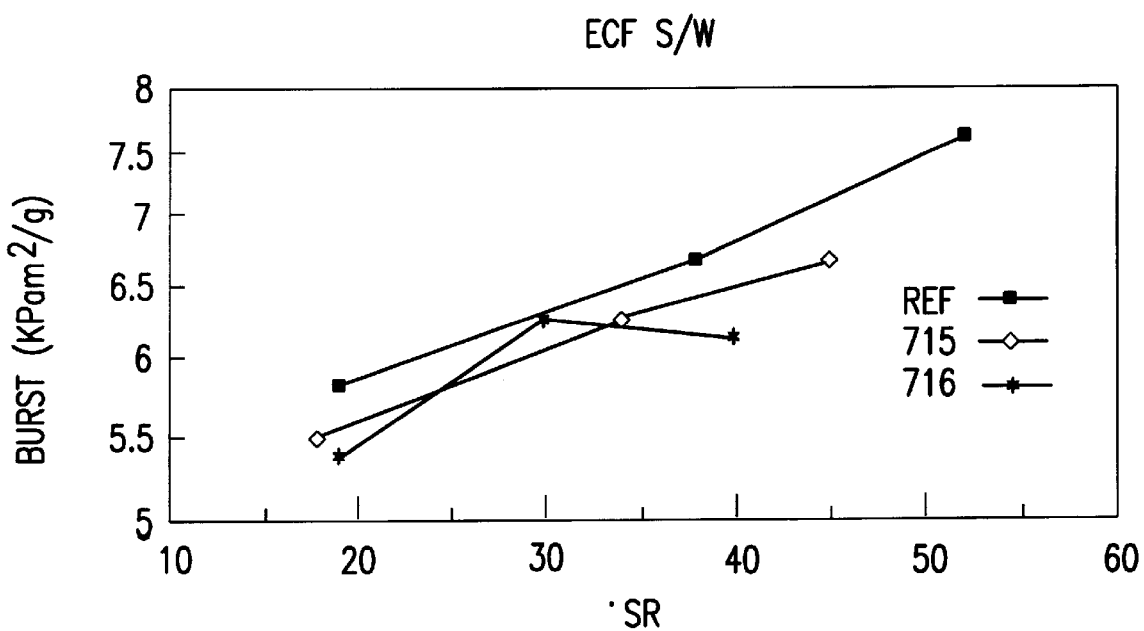
Figure 8A:
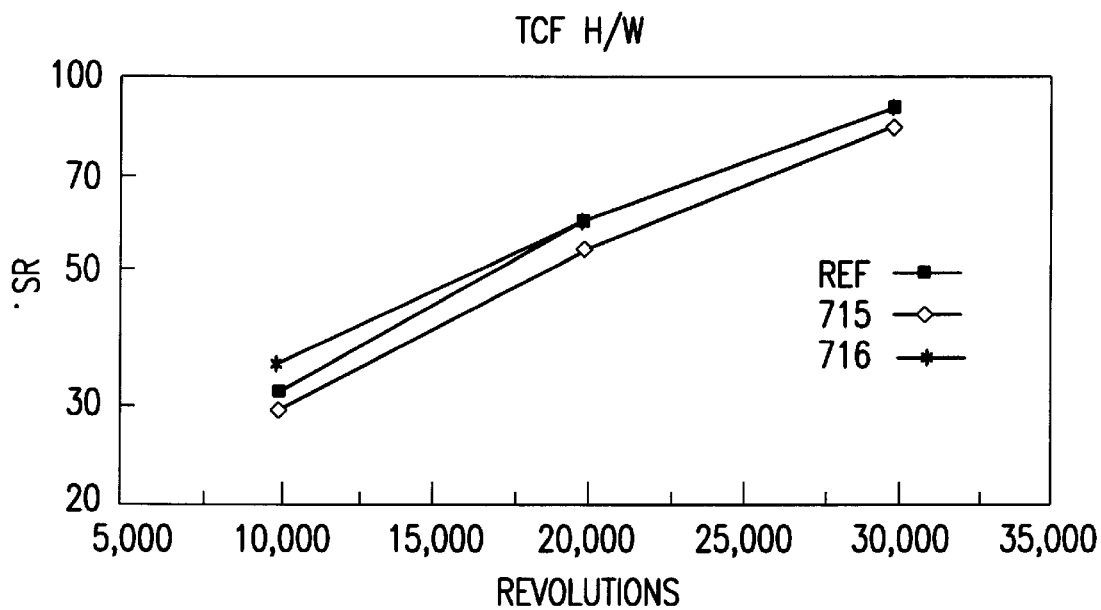
Figure 8B:
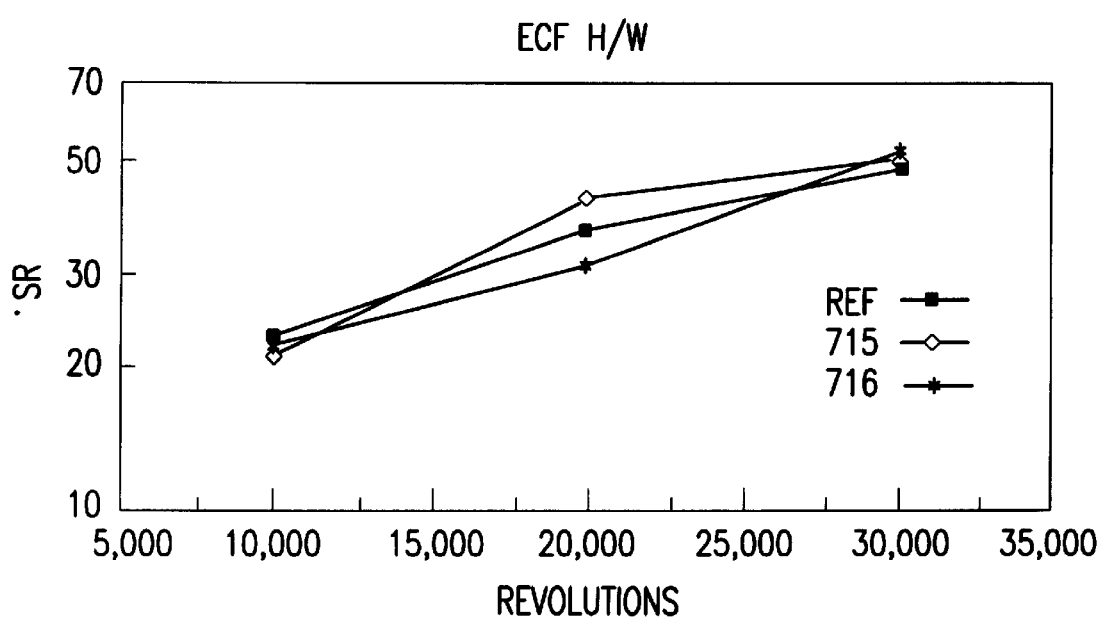
Figure 8C:
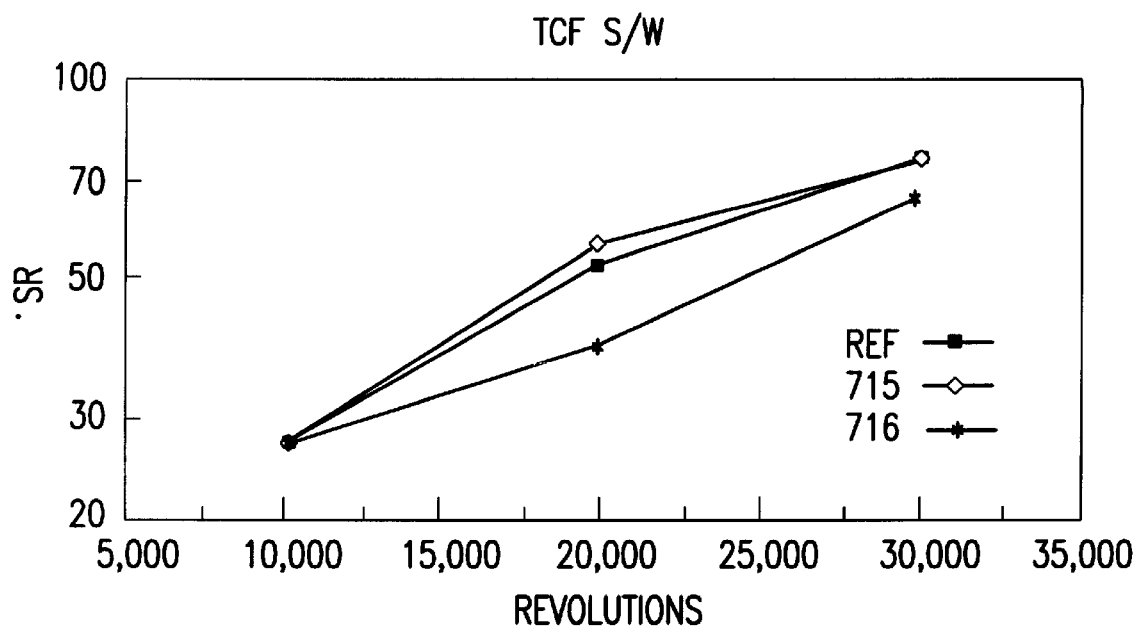
Figure 8D:
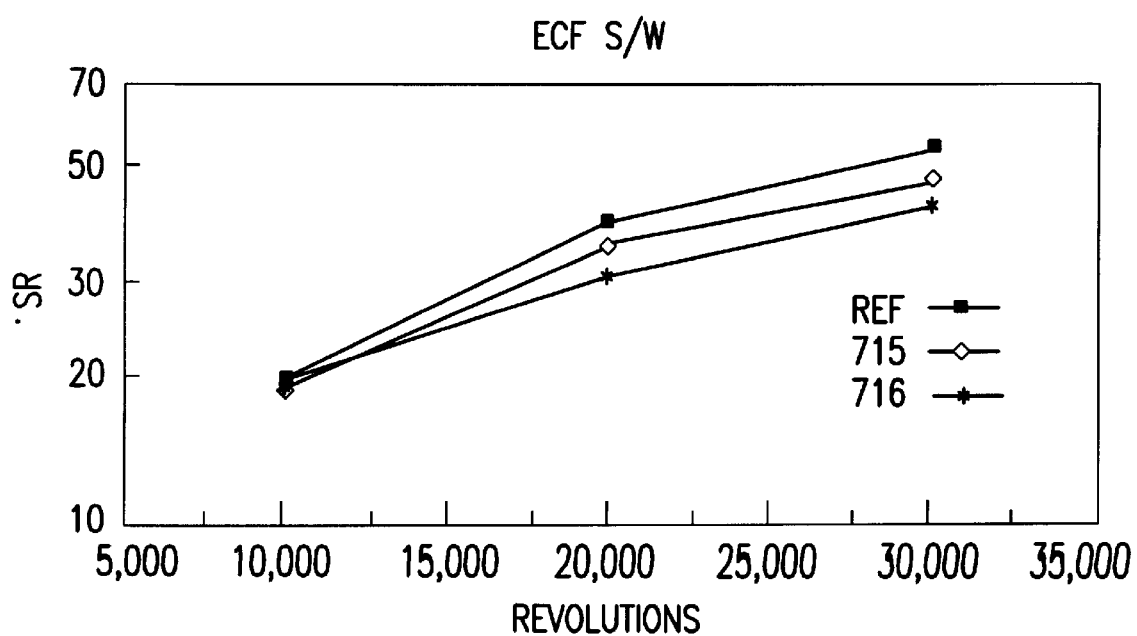

FIG. 3 shows the sequence of the xylanase domain of xynD from TG456 inserted in pJLA602 as a SphI-BamHI fragment.

EXAMPLE 11

Production and recovery of cloned xylanases

In order to obtain protein samples from the cloned F-type xylanases the *E.coli* clones were fermented in a 10.0 liter capacity LH fermenter (series 210). The culture was maintained at 30° C. until induction (42° C.) with continuous aeration (4.8 liters/min), agitation (500 rpm) and pH control (pH 7.1). The media used and other additions are given below:

| Luria Broth (for inoculum cultures): | |
|---|---|
| Tryptone | 10 g |
| Yeast Extract | 5 g |
| NaCl | 10 g |
| Water | to 1000 ml |
| BGM2 bulk growth medium for fermenter runs (quantities are for final medium, i.e. 2 batches of 8.5 liters): | |
| $NH_4Cl$ | 3.22 g |
| $KH_2PO_4$ | 1.05 g |
| $MgSO_4.7H_2C$ | 0.135 g |
| $K_2SO_4$ | 0.043 g |
| $FeSO_4.7H_2 0$ | 0.003 g |
| SL-10 Trace Elements | 1 ml |
| Tryptone | 10 g |
| Yeast Extract | 4.7 g |
| Glycerol | 34 ml |
| Water | to 1000 ml |

After the fermenter vessel, with approximately 6 liters of water in it, was sterilized by autoclaving at 121° C. for 30 minutes, it was cooled to 30° C. The media concentrate (8.5 fold concentrate) was pumped through a sterile 0.2 μm cartridge filter (Sartorius). Prior to inoculation the following additions were made:

| Antifoam (Bevaloid 5901) | 10 ml (autoclaved) |
|---|---|
| $CaCl_2$ (17 mg/ml stock) | 1 ml (autoclaved) |
| Ampicillin | 850 mg (filter sterilized) |
| Thiamine (JM101 cultures only) | 8.7 mg (filter sterilized) |

The liquid volume was then adjusted to. 8.5 liters. The pH of the media was adjusted to 7.1. Filter-sterilized air was sparged through the fermenter at a flow rate of 4.8 liters per minute. The fermenter temperature was held at 30° C. by hot and cold water circulation through finger probes. pH control was by addition of autoclaved NaOH (5M) or $H_4SO_4$ (2M). The fermenter stirrer speed was 500 rpm.

Inoculation was initiated with an aliquot (approximately 10.0 ml) of a fresh culture of the *E.coli* clone grown in Luria Broth with 100 μg/mi ampicillin at an $OD_{650}$ of 0.2 to 0.4. The cells were grown to an $OD_{650}$ of between 11 and 13 at 30° C., then they fed-batched with a medium concentrate, allowed to recover and grown to an $OD_{650}$ of between 14 and 16. They were subsequently induced by raising the temperature to 42° C.

The cells were harvested 4 hours after maximum $OD_{650}$ was reached. The cells were recovered by hollow fibre filtration (0.1 μm, Amicon) and resuspended in 50 mM Tris-HCl (pH 8.0), 7.5 mM EDTA, 7.5 mM β-mercaptoethanol, 0.02% PMSF, 1.0 μM pepstatin A, 0.02% DNase and 0.02% lysozyme and incubated at 4° C. for 1 hour (total volume of approximately 1 liter). The cells were sonicated on ice in 160 ml batches for 4–6 minutes in one minute blasts until lysed (monitored by microscopys). An aliquot of 56 mM PMSF (in isopropanol) was added (each addition equivalent to 160 μM) for each two minutes of sonication to a final concentration of no more than 1 mM PMSF. After lysis was complete, cell debris was removed by centrifugation. The supernatant was heat treated at 70° C. until obvious precipitation of protein occurred (usually about 20–30 minutes) and the denatured protein was removed by centrifugation. Prior to phenyl-sepharose chromatography, ammonium sulphate was added to the heat-treated supernatant to a final concentration of 1.0M (this is termed the 1° heat treatment extract). The cell pellet derived from the sonicated cells was re-extracted by suspension in 1.0 liter of 50 mM Tris-HCl (pH 8.0), 5 mM EDTA, 7 mM β-mercaptoethanol, followed by a second heat treatment at 70° C. for 15 minutes and the precipitated protein was again removed by centrifugation. This was found to extract an additional 20–40% of the xylanase and was termed 2° heat treatment extract. Ammonium sulphate was added to this 2° heat treatment extract to 1.0M and the 10 and 2° heat treatment extracts were pooled prior to phenyl-sepharose separation. Xylanase activity was step-eluted from the 1100 ml bed volume phenyl-sepharose column (after extensive washing with 1.0M ammonium sulphate and return to baseline) using 1.0M NaCl and the eluted protein was concentrated and desalted by ultrafiltration with a YM3 membrane (Amico). The final concentration of the preparations are 25 mM Tris-HCl (pH 8.0), 5 mM EDTA, 7 mM β-mercaptoethanol, approximately 250 mM NaCl, 20% glycerol and 0.05% sodium azide.

For production of the G-type xylanases the method was nearly identical to that described above except that HEPES buffer was used in place of TrisHCl for both the extraction (pH 8.0) and the desalting (pH 7.3) steps. The final preparation had a buffer composition of 50 mM HEPES, pH 7.3, 1 mM EDTA, 7 mM β-meraptoethanol, 0.05% sodium Azide, 20.0% glycerol and ±250 mM NaCl.

In total 6 F-type preparations (5 xynA and 1 xynB) and 2 G-type preparation of sufficient purity were obtained. For both the F-type and, the G-type preparation the protein concentration was determined by the standard BCA method (Pierce, Rockford, Ill., USA). The purity of the samples was roughly estimated by running an SDS-PAGE gel (Phast-system, Pharmacia, 20% gel) and comparing the thickness of the band at about 40 kDa for the F-type, and about 25 kDa for the G-type with the thickness of the bands of the impurities. The purity of the samples varied between 20 and 70% (Table 9).

TABLE 9

Purity of F-type and G-type xylanase preparations

| Enzyme | Purity (%) |
|---|---|
| TG53 xynA | 30 |
| TG53 xynD (G-type) | 20 |
| TG456 xynA | 70 |
| TG456 xynD (G-type) | 30 |
| TG457 xynA | 70 |
| TG479 xynA | 70 |
| TG631 xynA | 70 |
| TG631 xynB | 20 |

EXAMPLE 12

ECF bleaching results with cloned F- and G-type xylanases

ECF-bleaching was performed using oxygen delignified Kraft pulp from a Swedish pulp mill. The softwood (SW) pulp had a kappa number of 16.0 and the hardwood (HW) pulp a kappa number of 10.6. A XDED-sequence was used under conditions as presented in Table 10.

TABLE 10

Bleaching conditions

| STAGE | X | $D_0$ | E | $D_1$ |
|---|---|---|---|---|
| Cons | 10% | 10% | 10% | 10% |
| Time | 120 min | 60 min | 60 min | 120 min. |
| Temp | 65° C. | 60° C. | 60° C. | 70° C. |
| pH | 9 | ≅2.5 | ≅10 | ≅3.5 |
| Chemical Dosage | 15 μg xyl. protein/g pulp | chlorine multiple: 0.15 | NaOH: 7.2 kg/t (SW) 5.9 kg/t (HW) | aCl$_2$: 10 kg/t (S/HW) |

X = enzyme, $D_0$, $D_1$ = chlorine dioxide, E = extraction with NaOH.

The results of these experiments are presented in Table 11. It can be seen that the G-type xylanases perform significantly better as compared with the F-type xylanases, when compared on the basis of enzyme protein.

TABLE 11

ECF bleaching with cloned F- and G-type xylanases.

| | Delta brightness (% ISO) | |
|---|---|---|
| Enzyme | SW | HW |
| TG53xynA | 1.0[2] | 1.2[5] |
| TG53xynD (G-type) | 5.9[3]/6.8[4] | 3.0[6] |
| TG456xynA | 1.2[1]/0.7[2] | 1.0[5] |
| TG456xynD (G-type) | 4.3[3]/5.9[4] | 4.0[5]/2.1[6] |
| TG457xynA | 0[1] | 0[6] |
| TG479xynA | 0.3[2] | 0.3[5] |
| TG631xynA | 0[1] | 0[6] |
| TG631xynB | 0[2] | — |

[1]–[6]refer to six separate experiments. The reference ISO brightness values of these experiments were as follows: expt 1: 73.5; expt 2: 78.3; expt 3: 52.0; expt 4: 52.3; expt 5: 79:0; expt 6: 80.5.

EXAMPLE 13

ECF dose-response curves with cloned G-type xylanases

Using the same XDED bleaching sequence as described in Example 12 the dosage of the two G-type xylanases was varied. The results are shown in Table 12. Dosages of 1 to 3 μg/g pulp already give an increase in ISO brightness of at least two points.

TABLE 12

Dose-response curves of two G-type xylanases

| Enzyme | dosage (μg xyl/g pulp) | Brightness HW (XDED) | | Brightness SW (XDED) | | | |
|---|---|---|---|---|---|---|---|
| | | % ISO | Δ % ISO | % ISO | Δ % ISO | % ISO | Δ % ISO |
| TG456 xynD | 0 | 78.5 | — | 55.85 | — | 62.92 | — |
| | 1 | 80.73 | 2.23 | 56.80 | 0.95 | 65.73 | 2.81 |
| | 3 | 81.03 | 2.53 | 58.06 | 2.21 | 68.12 | 5.20 |
| | 6 | 80.99 | 2.49 | 59.20 | 3.35 | 68.32 | 5.40 |
| | 15 | | | | | 70.45 | 7.53 |
| TG3 xynD | 0 | 78.5 | — | 55.85 | — | 66.75 | — |
| | 1 | 79.73 | 1.23 | 57.28 | 1.43 | 69.04 | 2.29 |
| | 3 | 80.13 | 1.63 | 57.87 | 2.02 | 69.35 | 2.60 |
| | 6 | 81.32 | 2.82 | 58.23 | 2.38 | 69.92 | 3.17 |
| | 15 | | | | | 72.39 | 5.64 |

EXAMPLE 14

TCF bleaching results with cloned G-type xylanases

The two G-type xylanases were tested in a TCF bleaching sequence using the XQPP sequence as described in Example 15 (below). Oxygen delignified hardwood kraftpulp was used (30 g o.d. per sample). The dosage of the G-type xylanases was varied as indicated in Table 13. ISO brightness values obtained for each sample after X, P1 and P2 stages are given in Table 13. The value represent the average of duplicate samples.

TABLE 13

TCF bleaching - dose response experiment with G-type xylanases.

| Sample | dosage (μg protein/ g. pulp) | X brightness | P1 brightness | P2 brightness |
|---|---|---|---|---|
| Control | 0 | 50.3 | 79.5 | 81.0 |
| TG456 xynD | 15 | 53.8 | 81.8 | 84.3 |
|  | 6 | 52.9 | 81.0 | 83.8 |
| TG53 xynD | 15 | 55.2 | 82.2 | 85.1 |
|  | 6 | 53.6 | 82.7 | 85.1 |

The experiment was repeated using dosages of 3 and 6 μg protein per g pulp. Only the brightness values obtained after the P2 stage were determined. Results are presented in Table 14.

TABLE 14

TCF bleaching - dose response experiment with G-type xylanases

| Sample | dosage (μg protein/g pulp) | P2 brightness |
|---|---|---|
| Control | 0 | 84.5 |
| TG466 xynD | 6 | 85.5 |
|  | 3 | 86.5 |
| TG53 xynD | 6 | 86.1 |
|  | 3 | 86.8 |

EXAMPLE 15

ECF and TCF results, including paper properties

Xylanase samples were tested for bleaching effect in ECF & TCF bleaching of a Kraft H/W and a Kraft S/W pulp supplied from a Swedish pulp mill. The cloned TG456 xynD and TG53 xynD (in this Example referred to as 715 and 716, respectively) are compared with "no-enzyme" reference samples. The refining tests in a Lampen ball mill showed that 715 gave the overall best performance with considerable improvements in Tear Index and no significant loss in Tensile and Burst Indices.

Screening Protocol

| Hardwood | | Softwood | |
|---|---|---|---|
| 1. TCF Ref | QPP | 1. TCF Ref | QPP |
| 2. Enz 715 | XQPP | 2. Enz 715 | XQPP |
| 3. Enz 716 | XQPP | 3. Enz 716 | XQPP |
| 4. ECF Ref | No X DEDED | 4. ECF Ref | No X DEDED |
| 5. Enz 715 | XDEDED | 5. Enz 715 | XDEDED |
| 6. Enz 716 | XDEDED | 6. Enz 716 | XDEDED |
| 7. Chem Ref | DEDED | 7. Chem Ref | DEDED |

Unbleached pulp properties

| Pulp | Kappa No | % ISO Brightness | Viscosity dm$^3$/kg |
|---|---|---|---|
| Kraft H/W | 10.8 | 53 | 1104 |
| Kraft S/W | 16.1 | 36.4 | 1003 |

Bleaching parameters to be tested

| % ISO Brightness | Chemical consumption | Kappa No | Viscosity | Paper Strength |
|---|---|---|---|---|
| TCF | | | | |
| After X XQP XQPP | XQP XQPP | XQPP | XQPP | XQPP |
| ECF | | | | |
| After X XDE XDED XDEDED | XDE XDED XDEDED | XDE | XDEDED | XDEDED |

Bleaching conditions

A) TCF H/W & S/W (Same bleaching conditions for both pulps)

| Stage | X | Q | P | P |
|---|---|---|---|---|
| Consistency (%) | 10 | 9 | 10 | 10 |
| Time (mins) | 120 | 5*4 secs in mixer | 180 | 180 |
| Temp. (° C.) | 65 | 65 | 85 | 85 |
| pH | 9 | 4–5 | 10.5–11 | 10.5–11 |
| Enz Charge | 3 | — | — | — |
| EDTA Charge (kg/t) | — | 3 | — | — |
| NaOH Charge (kg/t) | — | — | 20 | 10 |
| $H_2O_2$ Charge (kg/t) | — | — | 20 | 10 |

B) ECF H/W

| Stage | X | D | E | D | E | D |
|---|---|---|---|---|---|---|
| Consistency (%) | 10 | 10 | 10 | 10 | 10 | 10 |
| Time (mins) | 120 | 60 | 60 | 120 | 60 | 180 |
| Temp (° C.) | 65 | 60 | 60 | 70 | 60 | 70 |
| pH | 9 | 2–3 | ~11.5 | 2.5–3 | ~11.5 | 4–5 |
| Enz Charge (μg/g) | 3 | — | — | — | — | — |
| aCl Charge (kg/t) | — | 0.18* Kappa = 19.4 for X ref & all X's 21.6 for Chem Ref | — | 18 | — | 8 |
| NaOH Charge (kg/t) | — | — | 11.6 for X ref & all X's 13 for Chem Ref | — | 10 | — |

C) ECF S/W

| Stage | X | D | E | D | E | D |
|---|---|---|---|---|---|---|
| Consistency (%) | 10 | 10 | 10 | 10 | 10 | 10 |
| Time (mins) | 120 | 60 | 60 | 120 | 60 | 180 |

-continued

| Temp (° C.) | 65 | 60 | 60 | 70 | 60 | 70 |
|---|---|---|---|---|---|---|
| pH | 9 | 2–3 | ~11.5 | 2.5–3 | ~11.5 | 4–5 |
| Enz Charge (μg/g) | 3 | — | — | — | — | — |
| aCl Charge (kg/t) | — | 0.18* Kappa = 28.8 for X ref & all X's 32 for Chem Ref | — | 18 | — | 8 |
| NaOH Charge (kg/t) | — | — | 17.3 for X ref & all X's 19.2 for Chem Ref | — | 10 | — |

The results obtained in the above experiments are present in Tables 15 (Hardwood) and 16 (Softwood).

TABLE 15

A summary of the Hardwood bleaching results

Hardwood

| | P2 % ISO | P2 Kappa | P2 Visc | Total P | |
|---|---|---|---|---|---|
| TCF Ref | 78.4 | 6.7 | 866 | 25.2 | |
| TCF 715 | 81 | 6.2 | 850 | 26.1 | ++− |
| TCF 716 | 81.7 | 6.2 | 740 | 27.7 | ++− |
| | D2 % ISO | XDE Kappa | D2 Visc | Total aCl | |
| ECF Ref | 88.6 | 4.6 | 1050 | 46.1 | |
| ECF 715 | 89.1 | 4.5 | 1035 | 44.8 | ++−+ |
| ECF 716 | 88.6 | 4.6 | 1040 | 45 | 00−+ |
| Chem Ref | 88.6 | 4.9 | 1020 | 47 | |

TABLE 16

A summary of the Softwood bleaching results.

Softwood

| | P2 % ISO | P2 Kappa | P2 Visc | Total P | |
|---|---|---|---|---|---|
| TCF Ref | 69.1 | 7.3 | 814 | 18.5 | |
| TCF 715 | 72.1 | 6.7 | 805 | 16 | ++−+ |
| TCF 716 | 71 | 6.7 | 833 | 16.7 | +++ |
| | D2 % ISO | XDE Kappa | D2 Visc | Total aCl | |
| ECF Ref | 85.5 | 4.6 | 941 | 54.5 | |
| ECF 715 | 86.5 | 4.4 | 935 | 54.4 | ++−0 |
| ECF 716 | 86.7 | 4.3 | 935 | 54.5 | ++−0 |
| Chem Ref | 87.5 | 3.7 | 962 | 57.3 | |

Verification of paper Properties

After all the sequences were fully bleached, 30 g samples were taken and refined in a Lampen ball mill for 10, 20 and 30 thousand revolutions. Schopper-Rieglers were measured, after which approximately 2 g sheets were made for Tensile Index, Porosity, Tear Index and Burst Index. The sheets were left to condition for 24 hours at 23° C. and 50% relative humidity. The results obtained are presented in FIGS. 4 to 8.

EXAMPLE 16 pH optimum, temperature optimum and thermostability of TG456 xynD

Activities were measured as described in Example 2, procedure 1, with oat spelt xylane as substrate. All assays were performed in 50 mM phosphate buffer, at the pH and temperature as indicated. The results are presented in FIGS. 9 and 10.

The TG456 xylanase D is much more thermostable than the reference enzyme Pulpzyme HB (Novo Nordisk), and it has a slightly higher pH optimum

We claim:

1. A purified and isolated G-type xylanase enzyme from a thermophilic microorganism, wherein the G-type xylanase has the following characteristics:
   (a) has significant delignifying activity at a temperature of at least 80° C. and at a pH of 9.0 or above; and
   (b) the encoding nucleotide sequence therefor comprises an internal consensus fragment (ICF) which has more than 80% sequence identity with the G-type internal consensus fragment, positions 295 to 623, of SEQ ID NO:12, or which has an amino acid sequence at least 70% identical with SEQ ID NO: 13.

2. A xylanase according to claim 1 having a half-life at 80° C. and pH 9.0 of more than 10 minutes.

3. A xylanase according to claim 1 characterized in that the thermophilic organism is anaerobic.

4. A xylanase according to claim 1 having a half-life of more than 10 minutes at 80° C. and at pH 7.0.

5. A xylanase according to claim 1 having a half-life of more than 10 minutes at 65° C. and at pH 9.0.

6. A xylanase according to claim 3 having a half-life of more than 10 minutes at 80° C. and at pH 7.0.

7. A xylanase according to claim 3 having a half-life of more than 10 minutes al 65° C. and at pH 9.0.

8. A xylanase according to claim 1 derived from one of the bacterial strains deposited under deposition number CBS 211.94, 212.94, 213.94, 214.94, 215.94 or 216.94.

9. A xylanase according to claim 4 derived from one of the bacterial strains deposited under deposition number CBS 211.94, 212.94, 213.94, 214.94, 215.94 or 216.94.

10. A xylanase according to claim 6 derived from one of the bacterial strains deposited under deposition number CBS 211.94, 212.94, 213.94, 214.94, 215.94 or 216.94.

11. A xylanase according to claim 5 derived from one of the bacterial strains deposited under deposition number CBS 211.94, 212.94, 213.94, 214.94, 215.94 or 216.94.

12. A xylanase according to claim 7 derived from one of the bacterial strains deposited under deposition number CBS 211.94, 212.94, 213.94, 214.94, 215.94 or 216.94.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iii) ANTI-SENSE: NO (vi) ORIGINAL SOURCE:
      (C) INDIVIDUAL ISOLATE: xynFA (xi) SEQUENCE DESCRIPTION: SEQ ID NO: 1:

CACACKCTKG TKTGGCA                              17

(2) INFORMATION FOR SEQ ID NO: 2:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (C) INDIVIDUAL ISOLATE: xynFB (xi) SEQUENCE DESCRIPTION: SEQ ID NO: 2:

CATACKTTKG TTTGGCA                                                 17

(2) INFORMATION FOR SEQ ID NO: 3:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (vi) ORIGINAL SOURCE:
          (C) INDIVIDUAL ISOLATE: xynR (xi) SEQUENCE DESCRIPTION: SEQ ID NO: 3:

TMGTTKACMA CRTCCCA                                                 17

(2) INFORMATION FOR SEQ ID NO: 4:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (C) INDIVIDUAL ISOLATE: GF (xi) SEQUENCE DESCRIPTION: SEQ ID NO: 4:

TATNTGRSTN TMTATGGWTG G                                            21

(2) INFORMATION FOR SEQ ID NO: 5:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (C) INDIVIDUAL ISOLATE: GR (xi) SEQUENCE DESCRIPTION: SEQ ID NO: 5:

CCGCTNCTTT GGTANCCTTC                                                         20

(2) INFORMATION FOR SEQ ID NO: 6:

(i) SEQUENCE CHARACTERISTICS:
        (A) LENGTH: 1065 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Extremophile
        (C) INDIVIDUAL ISOLATE: TG456

(ix) FEATURE:
        (A) NAME/KEY: CDS
        (B) LOCATION: 3..1058
        (D) OTHER INFORMATION: /product= "xylanase A"
            /gene= "xynA"

(xi) SEQUENCE DESCRIPTION: SEQ ID NO: 6:

```
CC ATG GAC CTT TAT TCA ATC TCA GAT GAA AAT TGG GGG CAG CCT GTG        47
   Met Asp Leu Tyr Ser Ile Ser Asp Glu Asn Trp Gly Gln Pro Val
   1               5                   10                  15

CCT GAT TAT AAA CTG CCA TCA CTT TGT GAA AAG TAC AAA AAC TAT TTC       95
Pro Asp Tyr Lys Leu Pro Ser Leu Cys Glu Lys Tyr Lys Asn Tyr Phe
                20                  25                  30

AAG ATT GGA GTT GCT GTG CCC TAC AGG GCT CTG ACA AAT CCA GTT GAT      143
Lys Ile Gly Val Ala Val Pro Tyr Arg Ala Leu Thr Asn Pro Val Asp
            35                  40                  45

GTG GAG ATG ATA AAA AGG CAT TTC AAC AGC ATA ACA CCG GAG AAC GAG      191
Val Glu Met Ile Lys Arg His Phe Asn Ser Ile Thr Pro Glu Asn Glu
        50                  55                  60

ATG AAA CCA GAG AGC CTT CAG CCT TAT GAA GGT GGT TTT AGC TTT AGC      239
Met Lys Pro Glu Ser Leu Gln Pro Tyr Glu Gly Gly Phe Ser Phe Ser
    65                  70                  75

ATT GCA GAT GAG TAT ATA GAT TTT TGC AAA AAG AAC AAT ATC TCA CTG      287
Ile Ala Asp Glu Tyr Ile Asp Phe Cys Lys Lys Asn Asn Ile Ser Leu
80                  85                  90                  95

CGA GGG CAC ACK CTT GTT TGG CAT CAG CAA ACC CCG AGC TGG TTC TTT      335
Arg Gly His Thr Leu Val Trp His Gln Gln Thr Pro Ser Trp Phe Phe
                100                 105                 110

ACA AAT CCT GAG ACG GGC GAA AAA CTT ACT AAC AGT GAG AAG GAC AAG      383
Thr Asn Pro Glu Thr Gly Glu Lys Leu Thr Asn Ser Glu Lys Asp Lys
            115                 120                 125

RAA ATA CTA TTG GAT AGG CTA AAG AAG CAC ATC CAG ACA GTT GTT GGC      431
Xaa Ile Leu Leu Asp Arg Leu Lys Lys His Ile Gln Thr Val Val Gly
        130                 135                 140

AGG TAT AAG GGG AAA GTA TAT GCA TGG GAC GTT GTG AAT GAG GCG ATT      479
Arg Tyr Lys Gly Lys Val Tyr Ala Trp Asp Val Val Asn Glu Ala Ile
    145                 150                 155

GAT GAG AAT CAG CCG GAT GGG TAT AGA AGA AGT GAC TGG TAC AAT ATC      527
Asp Glu Asn Gln Pro Asp Gly Tyr Arg Arg Ser Asp Trp Tyr Asn Ile
```

```
                    160                 165                 170                 175
TTR GGA CCG GAG TAC ATT GAA AAG GCA TTT ATC TGG GCG CAT GAA GCA              575
Xaa Gly Pro Glu Tyr Ile Glu Lys Ala Phe Ile Trp Ala His Glu Ala
                180                 185                 190

GAC CCG AAA GCA AAG CTT TTC TAC AAT GAC TAC AGT ACA GAA GAM CCA              623
Asp Pro Lys Ala Lys Leu Phe Tyr Asn Asp Tyr Ser Thr Glu Xaa Pro
            195                 200                 205

TAT AAA AGA GGG AAT TTA TAT ACA CTA ATT AAA AAY TTA AAA GCM AAA              671
Tyr Lys Arg Gly Asn Leu Tyr Thr Leu Ile Lys Asn Leu Lys Ala Lys
        210                 215                 220

GGT GTG CCA GTT CAT GGT GTT GGG CTT CAG TGT CAT ATT TCA CTT GAC              719
Gly Val Pro Val His Gly Val Gly Leu Gln Cys His Ile Ser Leu Asp
    225                 230                 235

TGG CCG GAT GTG AGT GAA ATC GAG GAG ACT GTC AAA TTA TTT AGC AGG              767
Trp Pro Asp Val Ser Glu Ile Glu Glu Thr Val Lys Leu Phe Ser Arg
240                 245                 250                 255

ATT CCA GGA CTT GAA ATA CAC TTC ACA GAA ATT GAT ATA AGT ATT GCT              815
Ile Pro Gly Leu Glu Ile His Phe Thr Glu Ile Asp Ile Ser Ile Ala
                260                 265                 270

AAA AAC ATG ACC GAT GAT GAT GCA TAT AAC CGC TAT CTT TTG ATT CAG              863
Lys Asn Met Thr Asp Asp Asp Ala Tyr Asn Arg Tyr Leu Leu Ile Gln
            275                 280                 285

CAG GCA CAA AAA TTA AAA GCA ATT TTT GAT GTT TTG AAA AAG TAC AGA              911
Gln Ala Gln Lys Leu Lys Ala Ile Phe Asp Val Leu Lys Lys Tyr Arg
        290                 295                 300

AAT GTA GTT ACA AGT GTT ACA TTC TGG GGA CTG AAG GAT GAT TAC TCA              959
Asn Val Val Thr Ser Val Thr Phe Trp Gly Leu Lys Asp Asp Tyr Ser
    305                 310                 315

TGG CTA CGG GGA GAT ATG CCA CTT TTA TTC GAT AAA GAC TAC CAG CCA             1007
Trp Leu Arg Gly Asp Met Pro Leu Leu Phe Asp Lys Asp Tyr Gln Pro
320                 325                 330                 335

AAG TTT GCG TTC TGG AGC TTA ATT GAC CCA TCA GTT GTC CCA AAA GAG             1055
Lys Phe Ala Phe Trp Ser Leu Ile Asp Pro Ser Val Val Pro Lys Glu
                340                 345                 350

TAATGGATCC                                                                   1065
```

(2) INFORMATION FOR SEQ ID NO: 7:

(i) SEQUENCE CHARACTERISTICS:
        (A) LENGTH: 351 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Asp Leu Tyr Ser Ile Ser Asp Glu Asn Trp Gly Gln Pro Val Pro
 1               5                  10                  15

Asp Tyr Lys Leu Pro Ser Leu Cys Glu Lys Tyr Lys Asn Tyr Phe Lys
                20                  25                  30

Ile Gly Val Ala Val Pro Tyr Arg Ala Leu Thr Asn Pro Val Asp Val
            35                  40                  45

Glu Met Ile Lys Arg His Phe Asn Ser Ile Thr Pro Glu Asn Glu Met
        50                  55                  60

Lys Pro Glu Ser Leu Gln Pro Tyr Glu Gly Gly Phe Ser Phe Ser Ile
65                  70                  75                  80

Ala Asp Glu Tyr Ile Asp Phe Cys Lys Lys Asn Asn Ile Ser Leu Arg
                85                  90                  95

Gly His Thr Leu Val Trp His Gln Gln Thr Pro Ser Trp Phe Phe Thr
```

```
              100                 105                 110
Asn Pro Glu Thr Gly Glu Lys Leu Thr Asn Ser Glu Lys Asp Lys Xaa
            115                 120                 125

Ile Leu Leu Asp Arg Leu Lys Lys His Ile Gln Thr Val Val Gly Arg
130                 135                 140

Tyr Lys Gly Lys Val Tyr Ala Trp Asp Val Val Asn Glu Ala Ile Asp
145                 150                 155                 160

Glu Asn Gln Pro Asp Gly Tyr Arg Arg Ser Asp Trp Tyr Asn Ile Xaa
                165                 170                 175

Gly Pro Glu Tyr Ile Glu Lys Ala Phe Ile Trp Ala His Glu Ala Asp
                180                 185                 190

Pro Lys Ala Lys Leu Phe Tyr Asn Asp Tyr Ser Thr Glu Xaa Pro Tyr
            195                 200                 205

Lys Arg Gly Asn Leu Tyr Thr Leu Ile Lys Asn Leu Lys Ala Lys Gly
210                 215                 220

Val Pro Val His Gly Val Gly Leu Gln Cys His Ile Ser Leu Asp Trp
225                 230                 235                 240

Pro Asp Val Ser Glu Ile Glu Glu Thr Val Lys Leu Phe Ser Arg Ile
                245                 250                 255

Pro Gly Leu Glu Ile His Phe Thr Glu Ile Asp Ile Ser Ile Ala Lys
                260                 265                 270

Asn Met Thr Asp Asp Ala Tyr Asn Arg Tyr Leu Leu Ile Gln Gln
            275                 280                 285

Ala Gln Lys Leu Lys Ala Ile Phe Asp Val Leu Lys Lys Tyr Arg Asn
            290                 295                 300

Val Val Thr Ser Val Thr Phe Trp Gly Leu Lys Asp Asp Tyr Ser Trp
305                 310                 315                 320

Leu Arg Gly Asp Met Pro Leu Leu Phe Asp Lys Asp Tyr Gln Pro Lys
                325                 330                 335

Phe Ala Phe Trp Ser Leu Ile Asp Pro Ser Val Val Pro Lys Glu
                340                 345                 350

(2) INFORMATION FOR SEQ ID NO: 8:

(i) SEQUENCE CHARACTERISTICS:
        (A) LENGTH: 1633 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Extremophile
        (C) INDIVIDUAL ISOLATE: TG456

(ix) FEATURE:
        (A) NAME/KEY: CDS
        (B) LOCATION: 1..1632
        (D) OTHER INFORMATION: /partial
            /product= "xylanase B"
            /gene= "xynB"

(xi) SEQUENCE DESCRIPTION: SEQ ID NO: 8:

TGT ACC ATA AAA TGG CAG CAA ACA GTT CCA TCT GGG GTT TGG ACA GAA    48
Cys Thr Ile Lys Trp Gln Gln Thr Val Pro Ser Gly Val Trp Thr Glu
  1               5                  10                  15
```

```
GTT TCT GGT TCA TAT ACA GTA CCA CAG ACA GCA ACC CAG CTC ATA TTC        96
Val Ser Gly Ser Tyr Thr Val Pro Gln Thr Ala Thr Gln Leu Ile Phe
             20                  25                  30

TAT GTG GAA TCG CCA AAT GCA ACA CTT GAC TTT TAC CTT GAC GAC TTT       144
Tyr Val Glu Ser Pro Asn Ala Thr Leu Asp Phe Tyr Leu Asp Asp Phe
         35                  40                  45

ACT GTA ATA GAC AAA AAC CCG GTT ACA ATA CCT GCT GCG GCA AAA GAG       192
Thr Val Ile Asp Lys Asn Pro Val Thr Ile Pro Ala Ala Ala Lys Glu
     50                  55                  60

CCA GAG TTG GAG ATT CCA TCA CTT TGC CAG CAA TAC AGC CAG TAC TTT       240
Pro Glu Leu Glu Ile Pro Ser Leu Cys Gln Gln Tyr Ser Gln Tyr Phe
 65                  70                  75                  80

TCA ATT GGT GTT GCA ATA CCA TAT AGA GTG CTC CAA AAC CCG GTA GAA       288
Ser Ile Gly Val Ala Ile Pro Tyr Arg Val Leu Gln Asn Pro Val Glu
             85                  90                  95

AGA GCA ATG GTT TTA AAG CAT TTC AAC AGT ATT ACT GCT GAA AAT GAG       336
Arg Ala Met Val Leu Lys His Phe Asn Ser Ile Thr Ala Glu Asn Glu
        100                 105                 110

ATG AAG CCC GAT GCT ATA CAA AGA ACA GAA GGG CAG TTC AAT TTC GAT       384
Met Lys Pro Asp Ala Ile Gln Arg Thr Glu Gly Gln Phe Asn Phe Asp
    115                 120                 125

GTT GCA GAC CAG TAT GTT GAC TTT GCA CAG AGC AAT AAT ATT GGA ATA       432
Val Ala Asp Gln Tyr Val Asp Phe Ala Gln Ser Asn Asn Ile Gly Ile
130                 135                 140

AGA GGT CAT ACA CTG GTT TGG CAT CAA CAA ACT CCA GAT TGG TTT TTC       480
Arg Gly His Thr Leu Val Trp His Gln Gln Thr Pro Asp Trp Phe Phe
145                 150                 155                 160

CAG CAT TCT GAC GGT TCG CCA CTT GAT CCA AAC AAT TCT GAA GAC AAG       528
Gln His Ser Asp Gly Ser Pro Leu Asp Pro Asn Asn Ser Glu Asp Lys
                165                 170                 175

CAG CTT TTG AGA AAT AGG TTA AAA ACA CAC ATT CAG ACA CTT GTT GGA       576
Gln Leu Leu Arg Asn Arg Leu Lys Thr His Ile Gln Thr Leu Val Gly
            180                 185                 190

AGA TAT GCA GAG AAA GTT TAT GCA TGG GAT GTT GTA AAT GAA GCA ATT       624
Arg Tyr Ala Glu Lys Val Tyr Ala Trp Asp Val Val Asn Glu Ala Ile
        195                 200                 205

GAT GAA AAT CAA CCG GAT GGA TAT AGA AGA AGT GAA TGG TAC AGA ATT       672
Asp Glu Asn Gln Pro Asp Gly Tyr Arg Arg Ser Glu Trp Tyr Arg Ile
    210                 215                 220

TTA GGA CCA ACT CCA GAA ACA GGC GGA ATA CCA GAG TAT ATA ATC CTT       720
Leu Gly Pro Thr Pro Glu Thr Gly Gly Ile Pro Glu Tyr Ile Ile Leu
225                 230                 235                 240

GCA TTC CAG TAT GCA CGG GAA GCT GAC CCG AAC GCA AAA CTT TTC TAC       768
Ala Phe Gln Tyr Ala Arg Glu Ala Asp Pro Asn Ala Lys Leu Phe Tyr
                245                 250                 255

AAC GAT TAC AGC ACT GAA AAT CCA AAG AAG AGA CAG TTT ATT TAC AAC       816
Asn Asp Tyr Ser Thr Glu Asn Pro Lys Lys Arg Gln Phe Ile Tyr Asn
            260                 265                 270

ATG GTC AAA GCT TTG CAT GAT AGA GGT CTC ATT GAT GGT GTT GGT CTG       864
Met Val Lys Ala Leu His Asp Arg Gly Leu Ile Asp Gly Val Gly Leu
        275                 280                 285

CAG GGA CAT ATT AAT GTG GAT TCG CCT GCA GTC AAA GAA ATA GAA GAT       912
Gln Gly His Ile Asn Val Asp Ser Pro Ala Val Lys Glu Ile Glu Asp
    290                 295                 300

ACA ATC AAT TTA TTC AGC ACA ATA CCG GGT CTT CAA ATT CAA ATA ACA       960
Thr Ile Asn Leu Phe Ser Thr Ile Pro Gly Leu Gln Ile Gln Ile Thr
305                 310                 315                 320

GAG CTT GAT ATC AGC GTA TAT ACA AGC AGC ACT CAG CAA TAT GAC ACA      1008
Glu Leu Asp Ile Ser Val Tyr Thr Ser Ser Thr Gln Gln Tyr Asp Thr
                325                 330                 335
```

```
TTA CCA CAG GAT ATT ATG ATT AAA CAG GCT TTA AAA TTC AAA GAG CTG     1056
Leu Pro Gln Asp Ile Met Ile Lys Gln Ala Leu Lys Phe Lys Glu Leu
            340                 345                 350

TTT GAA ATG TTA AAG CGC CAC AGC GAC AGA ATC ACA AAT GTT ACA CTT     1104
Phe Glu Met Leu Lys Arg His Ser Asp Arg Ile Thr Asn Val Thr Leu
            355                 360                 365

TGG GGT CTC AAA GAT GAT TAT CCA TGG CTG TCA AAA GAT AGA AGT AAC     1152
Trp Gly Leu Lys Asp Asp Tyr Pro Trp Leu Ser Lys Asp Arg Ser Asn
    370                 375                 380

TGG CCA CTG CTA TTT GAT AGT AAC TAC CAG GCA AAA TAC AAT TAC TGG     1200
Trp Pro Leu Leu Phe Asp Ser Asn Tyr Gln Ala Lys Tyr Asn Tyr Trp
385                 390                 395                 400

GCT ATT GTA GAA CCT TCG GTG TTG CCT GTT GCT ATA AAT AAG GGA TAT     1248
Ala Ile Val Glu Pro Ser Val Leu Pro Val Ala Ile Asn Lys Gly Tyr
                405                 410                 415

GCG AAC AAT GCA CAG CCA AGA ATT GAT GGG ATT ATG GAT AAA GAA TAC     1296
Ala Asn Asn Ala Gln Pro Arg Ile Asp Gly Ile Met Asp Lys Glu Tyr
            420                 425                 430

AAA GGA ACC ATT CCA CTT TCG GTT TTG AAT GAT GCA GGG CAG GAT ATT     1344
Lys Gly Thr Ile Pro Leu Ser Val Leu Asn Asp Ala Gly Gln Asp Ile
            435                 440                 445

GCT CAG GTA AGG GCA CTG TGG AGT GGC AAT GAG CTT TGT CTT TAT GTC     1392
Ala Gln Val Arg Ala Leu Trp Ser Gly Asn Glu Leu Cys Leu Tyr Val
    450                 455                 460

ACT GTA AAT GAT TCA AGT GTG GAT GCT AAC AAT GAT AGG GTT GTA ATT     1440
Thr Val Asn Asp Ser Ser Val Asp Ala Asn Asn Asp Arg Val Val Ile
465                 470                 475                 480

TTC ATT GAT CAG GAC AAT GGA AAG TTG CCA GAG TTA AAA GAT GAT GAC     1488
Phe Ile Asp Gln Asp Asn Gly Lys Leu Pro Glu Leu Lys Asp Asp Asp
                485                 490                 495

TTC TGG GTT TCA ATT TCG AGA AAT GGC ACA AAG AAT CAA TCC AAA ACT     1536
Phe Trp Val Ser Ile Ser Arg Asn Gly Thr Lys Asn Gln Ser Lys Thr
            500                 505                 510

GGC TAT GTA AAA GAT TAT GTA GTG TTA CAG CAA TTA AAT GGA TAT ACA     1584
Gly Tyr Val Lys Asp Tyr Val Val Leu Gln Gln Leu Asn Gly Tyr Thr
            515                 520                 525

ATG GAG GTT AAG CTG CTT TTA AAC AAC AGT TTA GCA ATT AAC ACA AAT     1632
Met Glu Val Lys Leu Leu Leu Asn Asn Ser Leu Ala Ile Asn Thr Asn
    530                 535                 540

A                                                                   1633

(2) INFORMATION FOR SEQ ID NO: 9:

(i) SEQUENCE CHARACTERISTICS:
        (A) LENGTH: 544 amino acids
        (B) TYPE: amino acid
        (D) TOPOLOGY: linear (ii) MOLECULE TYPE: protein (xi) SEQUENCE DESCRIPTION: SEQ ID NO: 9:

Cys Thr Ile Lys Trp Gln Gln Thr Val Pro Ser Gly Val Trp Thr Glu
  1               5                  10                  15

Val Ser Gly Ser Tyr Thr Val Pro Gln Thr Ala Thr Gln Leu Ile Phe
              20                  25                  30

Tyr Val Glu Ser Pro Asn Ala Thr Leu Asp Phe Tyr Leu Asp Asp Phe
          35                  40                  45

Thr Val Ile Asp Lys Asn Pro Val Thr Ile Pro Ala Ala Ala Lys Glu
      50                  55                  60
```

```
Pro Glu Leu Glu Ile Pro Ser Leu Cys Gln Gln Tyr Ser Gln Tyr Phe
 65                  70                  75                  80

Ser Ile Gly Val Ala Ile Pro Tyr Arg Val Leu Gln Asn Pro Val Glu
                 85                  90                  95

Arg Ala Met Val Leu Lys His Phe Asn Ser Ile Thr Ala Glu Asn Glu
            100                 105                 110

Met Lys Pro Asp Ala Ile Gln Arg Thr Glu Gly Gln Phe Asn Phe Asp
        115                 120                 125

Val Ala Asp Gln Tyr Val Asp Phe Ala Gln Ser Asn Asn Ile Gly Ile
130                 135                 140

Arg Gly His Thr Leu Val Trp His Gln Gln Thr Pro Asp Trp Phe Phe
145                 150                 155                 160

Gln His Ser Asp Gly Ser Pro Leu Asp Pro Asn Asn Ser Glu Asp Lys
                165                 170                 175

Gln Leu Leu Arg Asn Arg Leu Lys Thr His Ile Gln Thr Leu Val Gly
            180                 185                 190

Arg Tyr Ala Glu Lys Val Tyr Ala Trp Asp Val Val Asn Glu Ala Ile
        195                 200                 205

Asp Glu Asn Gln Pro Asp Gly Tyr Arg Arg Ser Glu Trp Tyr Arg Ile
210                 215                 220

Leu Gly Pro Thr Pro Glu Thr Gly Gly Ile Pro Glu Tyr Ile Ile Leu
225                 230                 235                 240

Ala Phe Gln Tyr Ala Arg Glu Ala Asp Pro Asn Ala Lys Leu Phe Tyr
                245                 250                 255

Asn Asp Tyr Ser Thr Glu Asn Pro Lys Lys Arg Gln Phe Ile Tyr Asn
            260                 265                 270

Met Val Lys Ala Leu His Asp Arg Gly Leu Ile Asp Gly Val Gly Leu
        275                 280                 285

Gln Gly His Ile Asn Val Asp Ser Pro Ala Val Lys Glu Ile Glu Asp
290                 295                 300

Thr Ile Asn Leu Phe Ser Thr Ile Pro Gly Leu Gln Ile Gln Ile Thr
305                 310                 315                 320

Glu Leu Asp Ile Ser Val Tyr Thr Ser Ser Thr Gln Gln Tyr Asp Thr
                325                 330                 335

Leu Pro Gln Asp Ile Met Ile Lys Gln Ala Leu Lys Phe Lys Glu Leu
            340                 345                 350

Phe Glu Met Leu Lys Arg His Ser Asp Arg Ile Thr Asn Val Thr Leu
        355                 360                 365

Trp Gly Leu Lys Asp Asp Tyr Pro Trp Leu Ser Lys Asp Arg Ser Asn
370                 375                 380

Trp Pro Leu Leu Phe Asp Ser Asn Tyr Gln Ala Lys Tyr Asn Tyr Trp
385                 390                 395                 400

Ala Ile Val Glu Pro Ser Val Leu Pro Val Ala Ile Asn Lys Gly Tyr
                405                 410                 415

Ala Asn Asn Ala Gln Pro Arg Ile Asp Gly Ile Met Asp Lys Glu Tyr
            420                 425                 430

Lys Gly Thr Ile Pro Leu Ser Val Leu Asn Asp Ala Gly Gln Asp Ile
        435                 440                 445

Ala Gln Val Arg Ala Leu Trp Ser Gly Asn Glu Leu Cys Leu Tyr Val
450                 455                 460

Thr Val Asn Asp Ser Ser Val Asp Ala Asn Asn Asp Arg Val Val Ile
465                 470                 475                 480

Phe Ile Asp Gln Asp Asn Gly Lys Leu Pro Glu Leu Lys Asp Asp Asp
```

```
                    485                 490                 495
Phe Trp Val Ser Ile Ser Arg Asn Gly Thr Lys Asn Gln Ser Lys Thr
            500                 505                 510

Gly Tyr Val Lys Asp Tyr Val Val Leu Gln Gln Leu Asn Gly Tyr Thr
            515                 520                 525

Met Glu Val Lys Leu Leu Leu Asn Asn Ser Leu Ala Ile Asn Thr Asn
            530                 535                 540

(2) INFORMATION FOR SEQ ID NO: 10:

(i) SEQUENCE CHARACTERISTICS:
        (A) LENGTH: 1125 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Extremophile
        (C) INDIVIDUAL ISOLATE: TG456

(ix) FEATURE:
        (A) NAME/KEY: CDS
        (B) LOCATION: 1..1125
        (D) OTHER INFORMATION: /partial
            /product= "xylanase C"
            /gene= "xynC"

(xi) SEQUENCE DESCRIPTION: SEQ ID NO: 10:
```

```
CGC GAG TTA TTA CTT TAT GTT GAG GCG CAA AAT GCA AAT TTG GCT TTC        48
Arg Glu Leu Leu Leu Tyr Val Glu Ala Gln Asn Ala Asn Leu Ala Phe
 1               5                  10                  15

TGG GTT GAT GAT TTA AAG ATT TAT GAT TTA TCC AAG CTG GCT GAA CCT        96
Trp Val Asp Asp Leu Lys Ile Tyr Asp Leu Ser Lys Leu Ala Glu Pro
                20                  25                  30

GAA TGG GAG ATA CCA TCT TTG ATA GAA AAG TAT AAA GAT TAT TTC AAA       144
Glu Trp Glu Ile Pro Ser Leu Ile Glu Lys Tyr Lys Asp Tyr Phe Lys
            35                  40                  45

GTA GGG GTA GCT TTG TCT TAC AAA AGC ATT GCT YCT GAT ACA GAG AAG       192
Val Gly Val Ala Leu Ser Tyr Lys Ser Ile Ala Xaa Asp Thr Glu Lys
 50                  55                  60

AAG ATG GTT TTG AAG CAT TTC AAT AGT ATT ACT GCA GGG AAT GAA ATG       240
Lys Met Val Leu Lys His Phe Asn Ser Ile Thr Ala Gly Asn Glu Met
 65                  70                  75                  80

AAA CCA TCA GAG TTA CTT ATC AGT GAA AAT AAT TAT AAC TTT AGT AAA       288
Lys Pro Ser Glu Leu Leu Ile Ser Glu Asn Asn Tyr Asn Phe Ser Lys
                85                  90                  95

GCA GAT GAA TTT GTA AAT TTT GCA ACA AGT AAC AAC ATT GCC ATC AGA       336
Ala Asp Glu Phe Val Asn Phe Ala Thr Ser Asn Asn Ile Ala Ile Arg
            100                 105                 110

GGT CAT ACA CTG GTT TGG CAT GAG CAA ACA CCC GAC TGG TTT TTC AAG       384
Gly His Thr Leu Val Trp His Glu Gln Thr Pro Asp Trp Phe Phe Lys
        115                 120                 125

GAT GCA AAT GGA AAT ACC TTG AGC AAG GAT GCA TTG CTA AGC AGA TTA       432
Asp Ala Asn Gly Asn Thr Leu Ser Lys Asp Ala Leu Leu Ser Arg Leu
130                 135                 140

AAG CAG TAT ATT TAT ACG GTA GTG GGA AGA TAT AAA GGG AAG GTT TAT       480
Lys Gln Tyr Ile Tyr Thr Val Val Gly Arg Tyr Lys Gly Lys Val Tyr
145                 150                 155                 160
```

```
GCA TGG GAT GTG GTA AAT RAA GCA ATA GAT GAA AGT CAA GGT AAT GGA      528
Ala Trp Asp Val Val Asn Xaa Ala Ile Asp Glu Ser Gln Gly Asn Gly
                165                 170                 175

TTC AGG AGA TCT AAC TGG TAC AAC ATT TGT GGT CCC GAA TAT ATT GAA      576
Phe Arg Arg Ser Asn Trp Tyr Asn Ile Cys Gly Pro Glu Tyr Ile Glu
            180                 185                 190

AAG GCT TTT ATA TGG GCA CAT GAR GCC GAT CCA GAC GCA AAA TTG TTT      624
Lys Ala Phe Ile Trp Ala His Glu Ala Asp Pro Asp Ala Lys Leu Phe
                195                 200                 205

TAC AAC GAT TAC AAC ACA GAA AAC AGT CAG AAG AGA CAG TTT ATT TMC      672
Tyr Asn Asp Tyr Asn Thr Glu Asn Ser Gln Lys Arg Gln Phe Ile Xaa
            210                 215                 220

AAC ATG ATT AAG AGT CTC AAG GAA AAA GGT GTT CCA ATT CAT GGA ATA      720
Asn Met Ile Lys Ser Leu Lys Glu Lys Gly Val Pro Ile His Gly Ile
225                 230                 235                 240

GGA TTG CGG TGT CAT ATA AAT CTT GAT TGG CCC TCG ATT AGC GAG ATA      768
Gly Leu Arg Cys His Ile Asn Leu Asp Trp Pro Ser Ile Ser Glu Ile
                245                 250                 255

GAG AAC ACC ATA AAA TTG TTC AGC TCT ATA CCT GGA TTG GAG ATA CAC      816
Glu Asn Thr Ile Lys Leu Phe Ser Ser Ile Pro Gly Leu Glu Ile His
            260                 265                 270

ATT ACG GAG CTT GAT ATG AGT TTT TAT CAG TGG GGT TCG AGT ACC AGT      864
Ile Thr Glu Leu Asp Met Ser Phe Tyr Gln Trp Gly Ser Ser Thr Ser
            275                 280                 285

TAT TCA ACG CCA CCM AGA GAT CTC CTG ATA AAA CAG GCA ATG AGA TAT      912
Tyr Ser Thr Pro Pro Arg Asp Leu Leu Ile Lys Gln Ala Met Arg Tyr
            290                 295                 300

AAG GAG TTA TTC GAT TTA TTT AAA AAG TAC AAT GTA ATA ACT AAT GTA      960
Lys Glu Leu Phe Asp Leu Phe Lys Lys Tyr Asn Val Ile Thr Asn Val
305                 310                 315                 320

ACA TTC TGG GGA CTA AAG GAT GAT TAC TCA TGG CTG AGT CAA AAC TTT     1008
Thr Phe Trp Gly Leu Lys Asp Asp Tyr Ser Trp Leu Ser Gln Asn Phe
                325                 330                 335

GGA AAA AGT GAT TAC CCG TTG TTA TTT GAT GGA AAC TAT AAG TCA AAA     1056
Gly Lys Ser Asp Tyr Pro Leu Leu Phe Asp Gly Asn Tyr Lys Ser Lys
            340                 345                 350

TAT GCC TTT TGG AGC CTG ATT GAG CCA ACT GTG GTG CCG GTT ACC GGT     1104
Tyr Ala Phe Trp Ser Leu Ile Glu Pro Thr Val Val Pro Val Thr Gly
            355                 360                 365

CAT AGC TGT TTT TGC GCC ATG                                         1125
His Ser Cys Phe Cys Ala Met
            370                 375
```

(2) INFORMATION FOR SEQ ID NO: 11:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO: 11:

```
Arg Glu Leu Leu Leu Tyr Val Glu Ala Gln Asn Ala Asn Leu Ala Phe
1               5                   10                  15

Trp Val Asp Asp Leu Lys Ile Tyr Asp Leu Ser Lys Leu Ala Glu Pro
                20                  25                  30

Glu Trp Glu Ile Pro Ser Leu Ile Glu Lys Tyr Lys Asp Tyr Phe Lys
            35                  40                  45

Val Gly Val Ala Leu Ser Tyr Lys Ser Ile Ala Xaa Asp Thr Glu Lys
        50                  55                  60
```

```
Lys Met Val Leu Lys His Phe Asn Ser Ile Thr Ala Gly Asn Glu Met
 65                  70                  75                  80

Lys Pro Ser Glu Leu Leu Ile Ser Glu Asn Asn Tyr Asn Phe Ser Lys
                 85                  90                  95

Ala Asp Glu Phe Val Asn Phe Ala Thr Ser Asn Asn Ile Ala Ile Arg
            100                 105                 110

Gly His Thr Leu Val Trp His Glu Gln Thr Pro Asp Trp Phe Phe Lys
            115                 120                 125

Asp Ala Asn Gly Asn Thr Leu Ser Lys Asp Ala Leu Leu Ser Arg Leu
        130                 135                 140

Lys Gln Tyr Ile Tyr Thr Val Val Gly Arg Tyr Lys Gly Lys Val Tyr
145                 150                 155                 160

Ala Trp Asp Val Val Asn Xaa Ala Ile Asp Glu Ser Gln Gly Asn Gly
                165                 170                 175

Phe Arg Arg Ser Asn Trp Tyr Asn Ile Cys Gly Pro Glu Tyr Ile Glu
            180                 185                 190

Lys Ala Phe Ile Trp Ala His Glu Ala Asp Pro Asp Ala Lys Leu Phe
        195                 200                 205

Tyr Asn Asp Tyr Asn Thr Glu Asn Ser Gln Lys Arg Gln Phe Ile Xaa
210                 215                 220

Asn Met Ile Lys Ser Leu Lys Glu Lys Gly Val Pro Ile His Gly Ile
225                 230                 235                 240

Gly Leu Arg Cys His Ile Asn Leu Asp Trp Pro Ser Ile Ser Glu Ile
                245                 250                 255

Glu Asn Thr Ile Lys Leu Phe Ser Ser Ile Pro Gly Leu Glu Ile His
            260                 265                 270

Ile Thr Glu Leu Asp Met Ser Phe Tyr Gln Trp Gly Ser Ser Thr Ser
        275                 280                 285

Tyr Ser Thr Pro Pro Arg Asp Leu Leu Ile Lys Gln Ala Met Arg Tyr
290                 295                 300

Lys Glu Leu Phe Asp Leu Phe Lys Lys Tyr Asn Val Ile Thr Asn Val
305                 310                 315                 320

Thr Phe Trp Gly Leu Lys Asp Asp Tyr Ser Trp Leu Ser Gln Asn Phe
                325                 330                 335

Gly Lys Ser Asp Tyr Pro Leu Leu Phe Asp Gly Asn Tyr Lys Ser Lys
            340                 345                 350

Tyr Ala Phe Trp Ser Leu Ile Glu Pro Thr Val Val Pro Val Thr Gly
        355                 360                 365

His Ser Cys Phe Cys Ala Met
370                 375

(2) INFORMATION FOR SEQ ID NO: 12:

(i) SEQUENCE CHARACTERISTICS:
        (A) LENGTH: 1244 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Extremophile
        (C) INDIVIDUAL ISOLATE: TG456
```

(ix) FEATURE:
    (A) NAME/KEY: CDS
    (B) LOCATION: 1..1107
    (D) OTHER INFORMATION: /partial
        /product= "xylanase D"
        /gene= "xynD"

(xi) SEQUENCE DESCRIPTION: SEQ ID NO: 12:

```
AAA GTC TTG CTG GCT GCT CTG ATG TGT GTT GTG TTG GCT AAT CCT TTT      48
Lys Val Leu Leu Ala Ala Leu Met Cys Val Val Leu Ala Asn Pro Phe
 1               5                  10                  15

TAT GCA CAG GCA GCC ATG ACA TTT ACC TCT AAT GCA ACT GGG ACA TAC      96
Tyr Ala Gln Ala Ala Met Thr Phe Thr Ser Asn Ala Thr Gly Thr Tyr
                20                  25                  30

GAT GGT TAC TAC TAC GAG TTG TGG AAG GAC ACA GGG AAT ACT ACC ATG     144
Asp Gly Tyr Tyr Tyr Glu Leu Trp Lys Asp Thr Gly Asn Thr Thr Met
            35                  40                  45

ACA GTT GAC ACA GGA GGA AGA TTT AGC TGT CAG TGG AGT AAC ATT AAC     192
Thr Val Asp Thr Gly Gly Arg Phe Ser Cys Gln Trp Ser Asn Ile Asn
        50                  55                  60

AAT GCA CTC TTC AGA ACA GGT AAA AAG TTT AGC ACT GCA TGG AAT CAG     240
Asn Ala Leu Phe Arg Thr Gly Lys Lys Phe Ser Thr Ala Trp Asn Gln
 65                  70                  75                  80

CTT GGG ACT GTA AAG ATT ACC TAC TCT GCT ACC TAC AAT CCA AAT GGC     288
Leu Gly Thr Val Lys Ile Thr Tyr Ser Ala Thr Tyr Asn Pro Asn Gly
                 85                  90                  95

AAT TCC TAT CTC TGC ATT TAT GGA TGG TCA AGA AAT CCA CTT GTT GAA     336
Asn Ser Tyr Leu Cys Ile Tyr Gly Trp Ser Arg Asn Pro Leu Val Glu
            100                 105                 110

TTT TAT ATC GTT GAA AGC TGG GGC TCA TGG CGT CCG CCC GGG GCA ACG     384
Phe Tyr Ile Val Glu Ser Trp Gly Ser Trp Arg Pro Pro Gly Ala Thr
        115                 120                 125

TCA CTT GGC ACT GTA ACA ATT GAT GGA GCA ACA TAT GAT ATT TAT AAG     432
Ser Leu Gly Thr Val Thr Ile Asp Gly Ala Thr Tyr Asp Ile Tyr Lys
130                 135                 140

ACA ACT CGT GTT AAT CAG CCA TCT ATC GAA GGA ACA AGA ACA TTT GAT     480
Thr Thr Arg Val Asn Gln Pro Ser Ile Glu Gly Thr Arg Thr Phe Asp
145                 150                 155                 160

CAG TAC TGG AGT GTT AGG ACA TCA AAG AGA ACA AGT GGT ACT GTT ACT     528
Gln Tyr Trp Ser Val Arg Thr Ser Lys Arg Thr Ser Gly Thr Val Thr
                165                 170                 175

GTA ACT GAT CAT TTC AAA GCA TGG GCT GCA AAA GGT TTG AAC CTG GGT     576
Val Thr Asp His Phe Lys Ala Trp Ala Ala Lys Gly Leu Asn Leu Gly
            180                 185                 190

ACA ATT GAC CAG ATT ACA CTC TGT GTG GAA GGY TAC CAR AGC AGC GGC     624
Thr Ile Asp Gln Ile Thr Leu Cys Val Glu Gly Tyr Gln Ser Ser Gly
        195                 200                 205

TCA GCA AAT ATA ACA CAG AAT ACA TTT ACT ATT GGT GGT TCG AGT AGT     672
Ser Ala Asn Ile Thr Gln Asn Thr Phe Thr Ile Gly Gly Ser Ser Ser
210                 215                 220

GGC TCA AGT AAT GGT TCA AAT AAC GGT TCA AAT GAT GGT TCC AAT GGA     720
Gly Ser Ser Asn Gly Ser Asn Asn Gly Ser Asn Asp Gly Ser Asn Gly
225                 230                 235                 240

GGA ACA AAT GCA GGA ATT TCA ACY GCA AGC AGG ATA GAA TGT GAA AGT     768
Gly Thr Asn Ala Gly Ile Ser Thr Ala Ser Arg Ile Glu Cys Glu Ser
                245                 250                 255

ATG TCG CTC AGC GGY CCT TAT GTT TCA AGA ATT ACT TAT CCA TTT AAT     816
Met Ser Leu Ser Gly Pro Tyr Val Ser Arg Ile Thr Tyr Pro Phe Asn
            260                 265                 270

GGT ATA GCA CTT TAT GCG AAC GGA GAT AGA GCA ACG GCA AAT GTA AAC     864
```

```
Gly Ile Ala Leu Tyr Ala Asn Gly Asp Arg Ala Thr Ala Asn Val Asn
            275                 280                 285

TTT TCA GCA AGC CGT AAC TAT ACT TTT AAA TTA CGT GGA TGT GGA AAT      912
Phe Ser Ala Ser Arg Asn Tyr Thr Phe Lys Leu Arg Gly Cys Gly Asn
        290                 295                 300

AAC AAT AAT TTG GCA TCA GTT GAT TTA CTG ATA GAT GGA AAG AAA GTA      960
Asn Asn Asn Leu Ala Ser Val Asp Leu Leu Ile Asp Gly Lys Lys Val
305                 310                 315                 320

GGT TCG TTC TAT TAT AAG GGA ACA TAT CCT TGG GAA GCY TCT ATA AAT     1008
Gly Ser Phe Tyr Tyr Lys Gly Thr Tyr Pro Trp Glu Ala Ser Ile Asn
                325                 330                 335

AAT GTG TAT GTA AGT GCA GGT ACC CAC AGA GWG GAG CTT GTA CTT TCT     1056
Asn Val Tyr Val Ser Ala Gly Thr His Arg Xaa Glu Leu Val Leu Ser
            340                 345                 350

GCT GAT AAT GGT ACA TGG GAT GTC TAT GCG GAT TAT TTG TTA ATA CAA     1104
Ala Asp Asn Gly Thr Trp Asp Val Tyr Ala Asp Tyr Leu Leu Ile Gln
        355                 360                 365

TGAAATTCGG AAATGTTTTT AAAAATACTG CTTCGRAGAA GCAGGTATTT TTTTATGTTC   1164

ACTATTATAA AGCGATTGAA GTCAGTCTTA GTTCATCCTA GTTGTTCTTC ARACCGRTCA   1224

TAGCTGTTTC CKGCGCCATG                                              1244

(2) INFORMATION FOR SEQ ID NO: 13:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO: 13:

Lys Val Leu Leu Ala Ala Leu Met Cys Val Val Leu Ala Asn Pro Phe
1               5                   10                  15

Tyr Ala Gln Ala Ala Met Thr Phe Thr Ser Asn Ala Thr Gly Thr Tyr
                20                  25                  30

Asp Gly Tyr Tyr Tyr Glu Leu Trp Lys Asp Thr Gly Asn Thr Thr Met
            35                  40                  45

Thr Val Asp Thr Gly Gly Arg Phe Ser Cys Gln Trp Ser Asn Ile Asn
    50                  55                  60

Asn Ala Leu Phe Arg Thr Gly Lys Lys Phe Ser Thr Ala Trp Asn Gln
65                  70                  75                  80

Leu Gly Thr Val Lys Ile Thr Tyr Ser Ala Thr Tyr Asn Pro Asn Gly
                85                  90                  95

Asn Ser Tyr Leu Cys Ile Tyr Gly Trp Ser Arg Asn Pro Leu Val Glu
            100                 105                 110

Phe Tyr Ile Val Glu Ser Trp Gly Ser Trp Arg Pro Pro Gly Ala Thr
        115                 120                 125

Ser Leu Gly Thr Val Thr Ile Asp Gly Ala Thr Tyr Asp Ile Tyr Lys
    130                 135                 140

Thr Thr Arg Val Asn Gln Pro Ser Ile Glu Gly Thr Arg Thr Phe Asp
145                 150                 155                 160

Gln Tyr Trp Ser Val Arg Thr Ser Lys Arg Thr Ser Gly Thr Val Thr
                165                 170                 175

Val Thr Asp His Phe Lys Ala Trp Ala Ala Lys Gly Leu Asn Leu Gly
            180                 185                 190

Thr Ile Asp Gln Ile Thr Leu Cys Val Glu Gly Tyr Gln Ser Ser Gly
        195                 200                 205
```

-continued

```
Ser Ala Asn Ile Thr Gln Asn Thr Phe Thr Ile Gly Gly Ser Ser Ser
    210                 215                 220

Gly Ser Ser Asn Gly Ser Asn Asn Gly Ser Asn Asp Gly Ser Asn Gly
225                 230                 235                 240

Gly Thr Asn Ala Gly Ile Ser Thr Ala Ser Arg Ile Glu Cys Glu Ser
                245                 250                 255

Met Ser Leu Ser Gly Pro Tyr Val Ser Arg Ile Thr Tyr Pro Phe Asn
                260                 265                 270

Gly Ile Ala Leu Tyr Ala Asn Gly Asp Arg Ala Thr Ala Asn Val Asn
            275                 280                 285

Phe Ser Ala Ser Arg Asn Tyr Thr Phe Lys Leu Arg Gly Cys Gly Asn
        290                 295                 300

Asn Asn Asn Leu Ala Ser Val Asp Leu Leu Ile Asp Gly Lys Lys Val
305                 310                 315                 320

Gly Ser Phe Tyr Tyr Lys Gly Thr Tyr Pro Trp Glu Ala Ser Ile Asn
                325                 330                 335

Asn Val Tyr Val Ser Ala Gly Thr His Arg Xaa Glu Leu Val Leu Ser
            340                 345                 350

Ala Asp Asn Gly Thr Trp Asp Val Tyr Ala Asp Tyr Leu Leu Ile Gln
        355                 360                 365
```